United States Patent [19]
Kirchhoff et al.

[11] Patent Number: 4,661,193
[45] Date of Patent: Apr. 28, 1987

[54] ADHESIVE COMPOSITIONS FOR ARYLCYCLOBUTENE MONOMERIC COMPOSITIONS

[75] Inventors: Robert A. Kirchhoff; Jo Ann Gilpin, both of Midland, Mich.

[73] Assignee: The Dow Chemical Company, Midland, Mich.

[21] Appl. No.: 771,052

[22] Filed: Aug. 30, 1985

Related U.S. Application Data

[63] Continuation-in-part of Ser. No. 644,836, Aug. 27, 1984, abandoned.

[51] Int. Cl.$^4$ .............................. C09J 3/14; C09J 5/06; C08F 132/08
[52] U.S. Cl. ............................... 156/307.3; 156/331.1; 156/334
[58] Field of Search .................... 156/276, 334, 331.1, 156/307.3, 327; 528/396, 422; 526/280, 281

[56] References Cited

U.S. PATENT DOCUMENTS

| | | | |
|---|---|---|---|
| 2,970,077 | 1/1961 | Groves | 156/307.3 |
| 3,265,640 | 8/1966 | Overhults | 528/396 |
| 3,347,978 | 10/1967 | Simon et al. | 156/276 |
| 3,981,762 | 9/1976 | Davis et al. | 156/307.3 |
| 4,466,850 | 8/1984 | Eichelberger et al. | 156/276 |

*Primary Examiner*—Donald Czaja
*Assistant Examiner*—J. Davis

[57] ABSTRACT

Two solid substrates are bonded together by using a functionally effective amount of an arylcyclobutene monomeric composition as an adhesive.

33 Claims, No Drawings

4,661,193

ADHESIVE COMPOSITIONS FOR ARYLCYCLOBUTENE MONOMERIC COMPOSITIONS

CROSS-REFERENCE TO RELATED APPLICATION

This is a continuation-in-part of copending U.S. application Ser. No. 644,836, filed on Aug. 27, 1984, now abandoned.

BACKGROUND OF THE INVENTION

This invention relates to adhesive compositions comprised of arylcyclobutene monomeric compositions.

Adhesive compositions are used in many industries to bond substrates together. Certain uses require that the adhesives employed therein possess certain high performance characteristics. For example, the aviation and aerospace industry requires that the adhesives possess bonding characteristics at temperatures much greater than 200° C. Similarly, the electronics industry also requires such temperature performance as well as low thermal expansion, water resistance and low shrinkage upon bonding. Particularly, useful adhesives in the electronics industry are die attach materials. Such materials permanently bond the silicone chips to the semi-conductor package. In the finished device, the die attach provides a conductive path to remove heat from the chip and to provide an electrical ground.

Recently, polymeric materials have been employed as adhesives. Popular polymeric adhesives are conductive epoxies, urethanes, conductive polyimides, and acrylic polymers. Conductive epoxies are low viscosity pastes containing about 70 percent silver. Other metals, for example copper, and nickel, can be employed to reduce material costs. Urethanes are chosen to bond plastics, rubbers and fabrics because of their excellent elastomeric properties such as abrasion, tear and shock resistance. Urethanes lose their bonding strength above about 100° C., so their use in applications where greater temperatures are encountered is not desirable.

Conductive polyimides comprise approximately 70 percent silver powder and a polyimide resin dissolved in an amide solvent. Some of the most popular polyimides are condensation polyimides from the reaction between benzophenonetetracarboxylic acid dianhydride and diamino benzophenone, and addition polyimides from ethanol and norbornene end-capped polyimides. A disadvantage associated with using polyimides is that their preparation produces volatile by-products and they contain organic solvents that are difficult to remove. If such organics vaporize or outgas they can cause degradation, as well as leaving voids in the final bond. A major problem of the polymeric adhesives is that they are brittle. The epoxies give low peel strength and exhibit poor thermal shock resistance. Another disadvantage of the known polymeric adhesives is that they fail at higher temperatures.

In view of the disadvantages of known methods, it would be desirable to provide an adhesive composition which can be employed to bond a variety of different solid substrates, wherein the bonding process does not produce the evolution of volatile gases. Moreover, an adhesive which can substantially retain its bonding properties at higher temperatures is also desirable.

SUMMARY OF THE INVENTION

This invention is a method for adhering a first solid substrate to a second solid substrate. The method comprises applying a functionally effective amount of a monomeric composition comprising an arylcyclobutene monomer to a surface of the first substrate. The surface containing the monomeric composition is contacted with a surface of the second substrate. The monomeric composition is then subjected to conditions sufficient to bond the two substrates.

This invention provides a method for bonding two substrates together wherein no volatile gases are produced during the bonding operation. The process is useful in bonding together a variety of materials such as, for example, metals to metals such as steel, aluminum and copper; metals to plastics; plastics to plastics; providing composites, and the like.

In another aspect, this invention is a die attach material composition comprising (a) a functionally effective amount of a monomeric composition comprising an arylcyclobutene monomer, and (b) an amount of an electrical conductive metal composition.

This invention provides an adhesive composition suitable as a die attach material which substantially retains its bonding characteristics at high temperatures. The composition of this invention is useful as a die attach material in attaching silicone chips to a circuit board, and also encapsulating integrated circuits.

DETAILED DESCRIPTION OF THE INVENTION

The substrates which can be bonded in this invention are those substrates which are solid at the polymerization and cure temperatures of the monomeric composition of this invention as well as at conditions of ordinary use. Typically, the substrates are solid between about 0° C. and 600° C., although any substrate which is solid at the polymerization and cure temperatures can be employed. It can readily be determined if a substrate is suitable by merely applying an amount of the monomeric composition, subjecting the composition to polymerization and preferably curing conditions, and testing as to whether the polymeric composition adheres to the substrate. The polymeric composition adheres to the substrate when the substrate can be inverted without causing the polymeric composition to separate from the substrate. Suitable substrates include thermoplastic and thermoset polymeric compositions, glass, metals, inorganic solids such as silicon dioxide, and the like.

The monomeric composition of this invention is a composition which contains an arylcyclobutene monomer in uncured form. The monomers are in uncured form when they contain unreacted polymerization sites. The monomeric composition can be exclusively in the monomer form or a mixture of monomer along with some amount of monomer in partially polymerized form. The monomeric composition can also contain other compositions such as, for example, other monomers copolymerizable with the arylcyclobutene monomers as well as compositions to modify the adhesive's properties. Such additives can be used to reduce the amount of thermal expansion, to improve the electrical and thermal conductivity, and the like. Suitable electrical and preferably thermal conductive compositions include electrical and preferably thermal conductive metals such as gold, silver, copper, and suitable compositions useful to reduce the thermal expansion are ceramic powders as well as glass fibers, and the like. Suitable ceramic powders are whitewares, refractories, fused alumina, silicon carbide, aluminum silicate fibers and the like.

The arylcyclobutene monomers are molecular compositions which contain at least one arylcyclobutene moiety in a pendant position. An arylcyclobutene moiety is in a pendant position when it is bonded to the molecule such that upon opening the cyclobutene ring, addition polymerization sites are provided. Typically, there are two types of arylcyclobutene monomers. These are mono-arylcyclobutene monomers and poly(arylcyclobutene) monomers. A mono-arylcyclobutene monomer contains only one arylcyclobutene moiety pendantly bonded to a molecular composition which comprises the the monomer unit. Preferred mono-arylcyclobutene monomers contain an ethylenically unsaturated hydrocarbon group, or other moiety which is reactive with the cyclobutene ring of the arylcyclobutene moiety. Examples of such moieties include another arylcyclobutene moiety, an acetylene group, a conjugated diene moiety or other moiety capable of undergoing addition polymerization reactions. Poly(arylcyclobutene) monomers contain two or more arylcyclobutene moieties pendantly bonded to the monomer unit. The two types can be prepared in similar methods, the main differences being that the mono-arylcyclobutene monomers are prepared from a molecular compound with only one reactive moiety while the poly(arylcyclobutenes) employ a compound with two or more reactive moieties; or at least twice as much of the equivalent amount of arylcyclobutene compound is employed to prepare the poly(arylcyclobutene) monomer. Because, of their multiple reactivity provided by the multiple arylcyclobutene moieties, poly(arylcyclobutene) monomeric compositions are preferred.

The mono-arylcyclobutene monomers can correspond to the formula

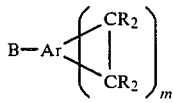

wherein B is a molecular composition corresponding to a bridging member of the poly(arylcyclobutene) monomers; Ar is an aryl moiety; R is separately in each occurrence hydrogen, or an electron-withdrawing substituent or an electron-donating substituent; and m is an integer of 1 or more.

The preferred mono-arylcyclobutene monomers which contain an ethylenically unsaturated hydrocarbon moiety, or a moiety which is reactive with the cyclobutene ring of an arylcyclobutene moiety can correspond to the same formula, wherein B is a molecular composition containing such moieties. The substituents of the formula will be described further in the description of the poly(arylcyclobutene) monomers.

The preferred mono-benzocyclobutene monomers can correspond to the formula

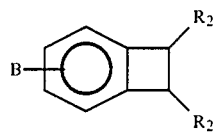

wherein B and R are described above. The molecular composition B can be bonded to any sit on the aryl noiety; however, because of reaction considerations the meta-sites are preferred.

Preferred molecular compositions for B include structures corresponding to the formulae

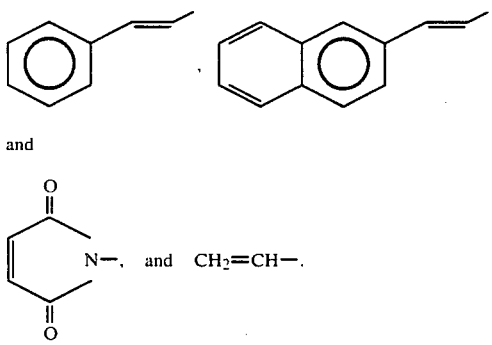

Poly(arylcyclobutene) monomers are a compound containing 2 or more arylcyclobutene moieties connected either by a direct bond or bridging merber. An arylcyclobutene moiety is an aryl group which contains one or more cyclobutene rings fused to the aromatic ring. Aryl moieties are those refered to as aromatic compounds containing $(4n+2)\pi$ electrons as described in Morrison & Boyd, *Organic Chemistry*, 3rd ed., 1973. Suitable aromatic moieties include benzene, naphthalene, phenanthrene, anthracene, pyridine, a biaryl moiety, or 2 or more aromatic moieties bridged by alkylene or cycloalkylene moieties. Preferred aromatic moieties are benzene, naphthalene, biphenyl, binaphthyl, diphenyl alkane or diphenyl cycloalkane moieties. The most preferred aromatic moiety is a benzene moiety.

The aryl moiety and cyclobutene ring can be substituted with a variety of substituents. Such substituents can be electron-donating or electron-withdrawing groups. Electron-donating groups are groups which draw electrons more than a hydrogen atom would if accompanying the same site. Electron-withdrawing groups are groups which donate an electron relative to a hydrogen atom. Examples of such substituents include cyano, halo, carboxy, hydrocarbyloxy, carbonyl, alkanoyl, aroyl, alkylsulfonyl, alkylsulfonoyl, amino, amido, or aryl groups.

The arylcyclobutene moieties are connected herein by a direct bond or bridging member. A bridging member (or molecular composition for mono-arylcyclobutene monomers) is a single nuclear or molecular chain supporting the arylcyclobutene moieties. Suitable bridging members comprise (1) a polyvalent inorganic moiety, or (2) a polyvalent organic moiety which can contain (a) one or more heteroatoms, comprising O, P, N, or S, or (b) one or more aromatic moieties. The bridging member or direct bond connects the arylcyclobutene moieties through the aryl moiety.

Polyvalent inorganic moiety refers to any inorganic moiety which can bond to 2 or more aryl moieties. Such polyvalent inorganic moieties can be covalently or ionically bonded to the aromatic moiety. Examples of polyvalent inorganic moieties include oxygen, phosphorus, phosphorus oxide, sulfur, nitrogen, polysiloxanes, polyvalent metals, sulfoxide, sulfone, a polyvalent metal bound to a polyvalent oxygenated moiety wherein the polyvalent oxygenated moiety can be further bound to an aryl moiety (for example, a polyvalent carboxylate salt). Preferred polyvalent inorganic moieties include oxygen, sulfur, polysiloxanes, and polyvalent metals bound to polyvalent oxygenated moieties.

The polyvalent organic bridging member can be any polyvalent organic moiety bonded to 2 or more aryl moieties. The organic bridging number can also contain one or more heteroatoms, comprising oxygen, nitrogen, phosphorus, silcon, or sulfur, or an organic moiety containing one or more aromatic moieties. Preferably, the polyvalent organic bridging member is a hydrocarbon poly-yl which is bonded to functionalized linking groups or a hydrocarbon poly-yl which contains an aromatic moiety. Hydrocarbon poly-yl is a hydrocarbon moiety which is bonded to 2 or more linking groups, wherein the hydrocarbon poly-yl can further contain one or more of the hereinbefore defined heteroatoms. Included within the term hydrocarbon are any organic moieties containing carbon and hydrogen atoms. Suitable hydrocarbons include the following organic moieties: alkanes, alkenes, alkynes, cycloalkanes, cycloalkenes, aromatic moieties, wherein aromatic is as defined hereinbefore, alkyl-substituted aromatic moieties, and aryl-substituted aliphatic moieties.

Linking group refers herein to any group which is capable of linking a hydrocarbon moiety to an aryl moiety. Linking groups include oxygen, sulfur, sulfoxide, sulfone, nitrogen, phosphorus, phosphorus oxide, oxycarbonyl, amido, carbonyl, carbonyldioxy, cyclic amido, carboxamidooxy, ureylene, carbonyloxycarbonyl, ammonium carboxylate salt and imido. Preferred linking groups are oxygen, sulfur, nitrogen, carbonyloxy, amido, carbonyldioxy, or cyclic amido. More preferred linking groups are carbonyloxy and amido.

Preferably the arylcyclobutene moieties are connected by direct bond or polyvalent organic moieties containing (1) one or more heteroatoms or (2) one or more aromatic moieties or (3) an ethylenically unsaturated hydrocarbon moiety. Most preferably, the arylcyclobutene moieties are connected by the bridging members comprising the polyvalent organic moieties containing (1) one or more heteroatoms or (2) one or more aromatic moieties.

In one preferred embodiment, the polyvalent bridging member is a divalent bridging member. More preferred divalent bridging members include ethylenically unsaturated hydrocarbon moieties, dicarbonyloxy hydrocarbylene, dicarboxamido hydrocarbylene, dicarbonyldioxy hydrocarbylene, dioxyhydrocarbylene, dithiohydrocarbylene or an aromatic moiety-containing hydrocarbylene group.

Even more preferred divalent organic bridging members are a vinyl moiety, dicarbonyloxyhydrocarbylene, dicarboxamidohydrocarbylene, di(carbonyloxy)hydrocarbylene, dioxyhydrocarbylene, and dithiohydrocarbylene.

Examples of polyvalent organic bridging members include the following: polyoxy(alk-poly-yl), polyoxy(ar-poly-yl), polyoxy(alkar-poly-yl), polyoxy(aralk-poly-yl), polythio(alk-poly-yl), polythio(ar-poly-yl), polythio(alkar-poly-yl), polythio(aralk-poly-yl), polyamido(alk-poly-yl), polyamido(ar-poly-yl), polyamido(alkar-poly-yl), polyamido(aralk-poly-yl), polycarbonyloxy(alk-poly-yl), polycarbonyloxy(ar-poly-yl), polycarbonyloxy(alkar-poly-yl), polycarbonyloxy(aralk-poly-yl), polycarbonyldioxy(alk-poly-yl), polycarbonyldioxy(ar-poly-yl), polycarbonyldioxy(alkar-poly-yl), polycarbonyldioxy(aralk-poly-yl), polyamino(alk-poly-yl), polyamino(ar-poly-yl), polyamino(alkar-poly-yl), polyamino(aralk-poly-yl), polycyclicimido(ar-poly-yl), polycyclicimido(alkar-poly-yl), polycyclicimido(aralk-poly-yl), polycarbonyl(alk-poly-yl), polycarbonyl(ar-poly-yl), polycarbonyl(alkar-poly-yl), polycarbonyl(aralk-poly-yl), polyimido(alk-poly-yl), polyimido(ar-poly-yl), polyimido(alkar-poly-yl), polyimido(aralk-poly-yl), polyureylene(alk-poly-yl), polyureylene(ar-poly-yl), polyureylene(alkar-poly-yl), polyureylene(aralk-poly-yl), polycarboxamideoxy(alk-poly-yl), polycarboxamideoxy(ar-poly-yl), polycarboxamideoxy(alkar-poly-yl), polycarboxamideoxy(aralk-poly-yl), ar-poly-yl, alkaryl-poly-yl, aralkyl-poly-yl, and alkenoic-poly-yl.

Hydrocarbyl means herein an organic moiety containing carbon and hydrogen atoms. The term hydrocarbyl includes the following organic moieties: alkyl, alkenyl, alkynyl, cycloalkyl, cycloalkenyl, aryl, aliphatic and cycloaliphatic aralkyl and alkaryl. Aliphatic refers herein to straight- and branched-, and saturated and unsaturated, hydrocarbon chains, that is, alkyl, alkenyl or alkynyl. Cycloaliphatic refers herein to saturated and unsaturated cyclic hydrocarbons, that is, cycloalkenyl and cycloalkyl. The term aryl refers herein to cyclic hydrocarbons containing $(4n+2)\pi$ electrons, such as biaryl, biphenylyl, phenyl, naphthyl, phenanthrenyl, anthracenyl and two aryl groups bridged by an alkylene group. Alkaryl refers herein to an alkyl-, alkenyl- or alkynyl-substituted aryl substituent wherein aryl is as defined hereinbefore. Aralkyl means herein an alkyl, alkenyl or alkynyl group substituted with an aryl group, wherein aryl is as defined hereinbefore. $C_{1-20}$ alkyl includes straight- and branched-chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. $C_{1-5}$ alkyl includes methyl, ethyl, propyl, butyl and pentyl.

Cycloalkyl refers to alkyl groups containing one, two, three or more cyclic rings. Cycloalkenyl refers to mono-, di- and polycyclic groups containing one or more double bonds. Cycloalkenyl also refers to cycloalkenyl groups wherein two or more double bonds are present.

Hydrocarbylene refers herein to a divalent hydrocarbon moiety. Poly-yl refers herein to a polyvalent moiety, for example, ar-poly-yl refers to a polyvalent aromatic moiety. Poly refers herein to two or more.

Preferred arylcyclobutenes monomers (which include the mono-arylcyclobutene monomers discussed above) can correspond to the formula

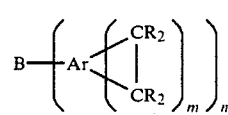

I wherein B is a direct bond or bridging member which comprises (1) a polyvalent inorganic moiety, or (2) a polyvalent organic moiety which can contain (a) one or more heteroatoms comprising oxygen, sulfur, nitrogen, silicon, or phosphorus, or (b) one or more aromatic moieties; Ar is an aromatic moiety which can be substituted; R is separately in each occurrence hydrogen or an electron-withdrawing or electron-donating substituent; m is an integer of 1 or more; and n is an integer of 1 or more, with the proviso that B can only be a direct bond wherein n is 2.

In one preferred embodiment, the aromatic moiety is benzene and m is 1. In this preferred embodiment, the arylcyclobutenes monomer can be referred to as a benzocyclobutene monomer. Preferred benzocyclobutene monomers can correspond to the formula

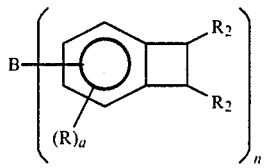
II wherein a is separately in each occurrence the integer 0, 1, 2, or 3; and B, R, and n are as defined hereinbefore. In formula II, a is preferably 0 or 1, and most preferably 0. R is preferably hydrogen, a cyano, or hydrocarbyloxycarbonyl group; more preferably hydrogen or cyano; and most preferably hydrogen.

In one embodiment, B can be a polyvalent inorganic bridging member, wherein inorganic bridging member is as defined hereinbefore. Preferable inorganic polyvalent moieties include —O—, —S—, —P—, —N—,

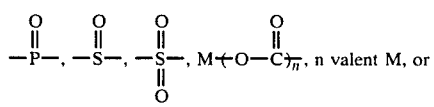

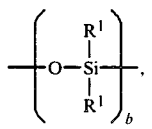

wherein M is a metal; $R^1$ is an alkyl, aryl, alkaryl, aralkyl, alkoxy, aryloxy, alkaryloxy or aralkyloxy; and b is an integer of 1 or greater. More preferable polyvalent inorganic bridging nembers include —O—, —S—, —N—,

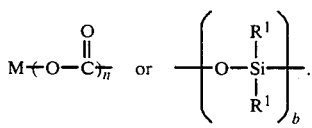

Polyvalent organic moiety is as defined hereinbefore. Preferred polyvalent organic moieties include those wherein B is (a) the formula X—(Z—)$_n$ wherein X is a hydrocarbon poly-yl moiety wherein the hydrocarbon poly-yl can contain a heteroatom of oxygen, phosphorus, sulfur or nitrogen, and Z is a functionalized linking moiety; or (b) a hydrocarbon poly-yl containing one or more aromatic moieties. Hydrocarbon poly-yl is as defined hereinbefore. The functionalized linking moiety is as defined hereinbefore. Preferably, X is an alk-poly-yl, cycloalk-poly-yl, ar-poly-yl, alkar-poly-yl, a biaromatic alkylene or cycloalkylene bridged poly-yl. More preferably, X is —(CH$_2$—)$_p$,

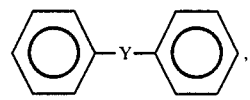

a phenylene, biphenylene, or cycloalkylene wherein Y is a $C_{1-20}$ straight-or branched-chain moiety or a cycloalkylene moiety and p is an integer of between about 2 and 20, inclusive. Most preferably X is —(CH$_2$—)$_p$, CH=CH—, phenylene,

Preferably, Z is O, S, N, P,

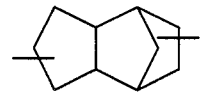

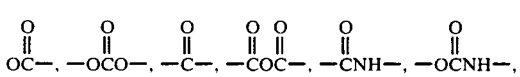

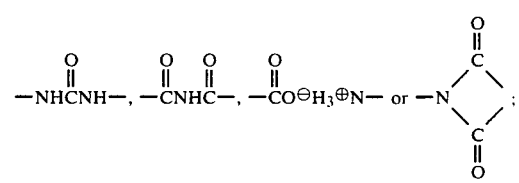

more preferably, O, S,

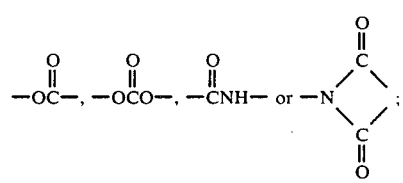

and more preferably

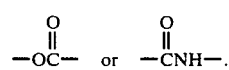

Preferred poly(benzocyclobutene) monomers include those with carboxamide-linking groups wherein the bridging members correspond to the formulae

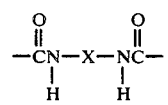

and

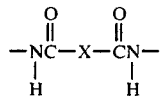

those with carbonyloxy-linking groups wherein the bridging members correspond to the formulae

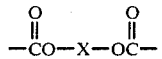

and

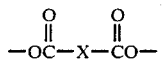

those with carbonyldioxy-linking groups wherein the bridging member corresponds to the formula

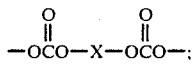

those with oxygen-linking groups wherein the bridging member corresponds to the formula

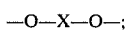

those with sulfur-linking groups wherein the bridging member corresponds to the formula

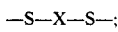

and those with cyclic imid-linking groups wherein the bridging member corresponds to the formula

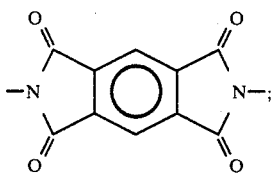

wherein X is as hereinbefore defined. More preferred bridging members which contain carboxamide-linking groups correspond to the following formulae:

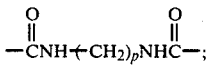

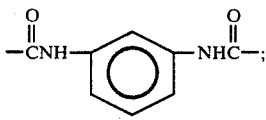

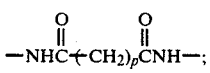

and

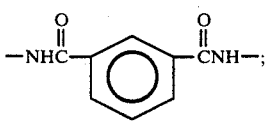

wherein p is as defined hereinbefore and p is an integer of 1 or greater, preferably between 1 and 20. More preferred bridging members with carbonyloxy-linking groups correspond to the formulae:

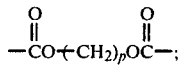

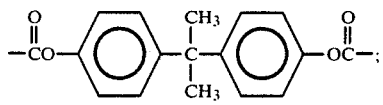

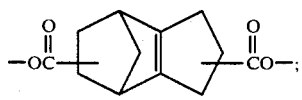

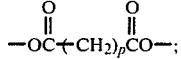

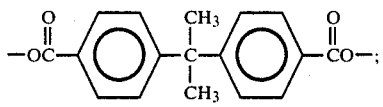

and

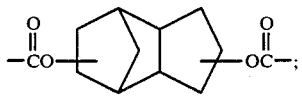

wherein p is as defined hereinbefore. Preferred bridging members for ultraviolet radiation polymerization are the benzophenones, for example, corresponding to the formula

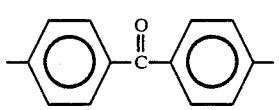

More preferred bridging members wherein the linking group is carbonyldioxy include those which correspond to the following formulae

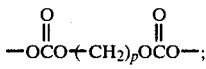

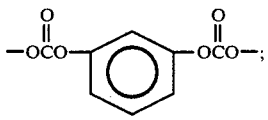

and

-continued

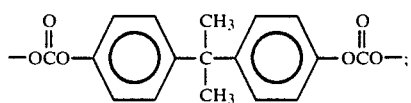

wherein p is as defined hereinbefore. More preferred bridging members with oxygen-linking groups include which correspond to the formulae

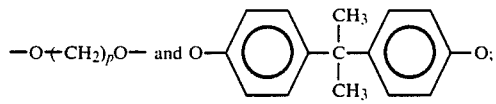

wherein p is as defined hereinbefore. More preferred bridging members with sulfur-linking groups include those which correspond to the formula

wherein p is as defined hereinbefore. More preferred bridging members with cyclic imid-linking groups include those which correspond to the formula

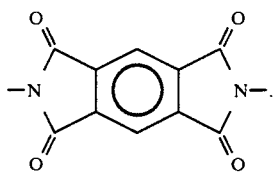

In one preferred embodiment, the polyvalent organic bridging member contains one or more aromatic moieties, and such bridging member generally corresponds to the formula

wherein Ar is as hereinbefore defined; $R^3$ is separately in each occurrence an alkylene, cycloalkylene or alkenylene moiety; r is independently in each occurrence 0 or 1; and q is 1 or greater. $R^3$ is preferably a $C_{1-20}$ alkylene or $C_{1-20}$ alkenylene. $R^3$ is more preferably $C_{1-10}$ alkylene or $C_{1-10}$ alkenylene. $R^3$ is even more preferably $C_{1-4}$ alkylene or $C_{1-4}$ alkenylene, with —CH=CH— being most preferred. Preferably q is between 1 and 20, most preferably between 1 and 10. In a more preferred embodiment, the aromatic moiety hydrocarbon poly-yl bridging member corresponds to the formula

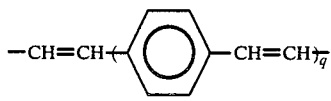

wherein q is as hereinbefore defined.

The arylcyclobutene monomers useful as adhesives in this invention can be prepared by several synthesis schemes. The preferred methods of preparation of such monomers are described hereinafter.

In one synthesis scheme, an alkyl-substituted aromatic compound which is further substituted with an aryl deactivating substituent is chloroalkylated in a position ortho to the alkyl group. In the preferred embodiment wherein the aromatic compound is benzene, the starting material can correspond to the following formula

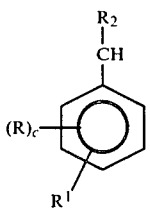

wherein R is as defined hereinbefore; $R^1$ is any aryl deactivating substituent; and c is an integer of 0, 1, 2, or 3. The alkyl-substituted aromatic compound can be chloroalkylated by contacting the alkyl aromatic compound with a chloroalkylating agent, and optionally, thionyl chloride in the presence of an iron chloride catalyst to provide a product which contains a chloroalkyl group ortho to the alkyl substituent. In the embodiment wherein the aromatic compound is a benzene ring, the product can correspond to the formula

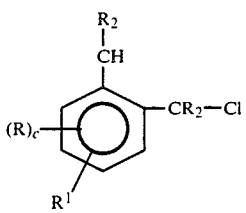

wherein R is as defined hereinbefore and $R^1$ is an aryl deactivating group. $R^1$ is preferably a hydrocarbyloxycarbonyl, carboxamide, hydrocarbylcarbonyl, carboxylate, halocarbonyl, nitrile, nitro, sulfone or sulfoxide group. $R^1$ is more preferably a halo, a halocarbonyl or hydrocarbyloxycarbonyl group, with hydrocarbyloxycarbonyl being the most preferred group. Preferably c is 0 or 1, most preferably 0.

In this process the chloroalkylating agent is preferably chloromethyl methyl ether, although other chloroalkylating agents such as bis(chloromethyl) ether could be used. At least a 2:1 molar excess of the chloroalkylating agent to the alkyl-substituted aromatic compound is needed. It is preferable to use at least about a 3:1 ratio of chloroalkylating agent to alkyl aromatic compound. The catalyst is ferric chloride ($FeCl_3$) or ($SnCl_4$) while an optional reaction promoter is thionyl chloride. The catalyst can be present in between about 0.05 and 1.0 mole per mole of alkyl aromatic. More preferably between about 0.05 and 0.6 mole of catalyst are present for each mole of alkyl aromatic compound. Preferably at least about 0.1 mole of thionyl chloride per mole of alkyl aromatic is used, more preferably between about 0.1 and 0.8 mole per mole of alkyl aromatic.

This process can be performed at a temperature of between about 40° C. and 80° C., preferably about 40° C. and 60° C. Below about 40° C., the reaction rate is low. The boiling point of some of the components of the reaction mixture starts at about 60° C.

This process can be performed by contacting the alkyl aromatic compound with the chloroalkylating agent, catalyst and optional reaction promoter in a suitable solvent. Suitable solvents are those solvents which are inert to the chloroalkylation conditions, and can include chlorinated hydrocarbon solvents. Thereafter the reaction mixture is heated to the appropriate temperature. The product can be recovered by quenching the reaction mixture with alcohols or water to inactivate the chloroalkylating agents remaining, stripping off the volatiles and washing out the catalyst with water. The product thereafter is recovered by distillation or recrystallization.

The ortho chloroalkylated alkyl aromatic compounds can be converted to aromatic compounds with cyclobutene rings fused thereto, by pyrolysis. This is achieved by contacting the ortho chloroalkylated alkyl aromatic compound with at least 2 times its weight of a suitable diluent, and thereafter passing the mixture through a reactor at a temperature of 550° C. or greater and a pressure of between about atmospheric and 25 mm of mercury. Suitable diluents are generally substituted aromatic compounds which are inert to the chloroalkylated alkyl aromatic compound and are stable at pyrolysis temperatures. Examples of suitable diluents are benzene, toluene, xylenes, chlorobenzenes, nitrobenzenes, methylbenzoates, phenyl acetate or diphenyl acetate. Preferred diluents are the xylenes or nitrogen gas. Preferable temperatures are between about 650° C. and 750° C. Preferable pressures are between about 100 and 10 mm of mercury. In a preferred embodiment, the reaction mixture is passed through a hot tube packed with an inert material, for example, quartz chips or stainless steel helices. The product can be recovered by distillation. The product wherein the aromatic compound is benzene can correspond to the formula

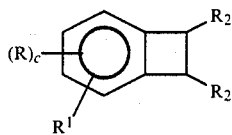

wherein R, and $R^1$ are as hereinbefore defined.

In the preferred embodiment wherein $R^1$ is a hydrocarbyloxy carbonyl moiety, the hydrocarbyloxy carbonyl moiety can be converted to a carboxylate moiety by contacting the substituted (arylcyclobutene) compound with at least a molar equivalent of alkali metal hydroxide in an alkanol-water solvent system. In the embodiment wherein the aromatic moiety is benzene, the product can correspond to the formula

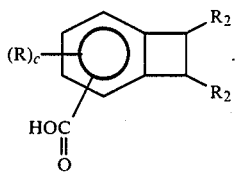

Thereafter the carboxylate-substituted (arylcyclobutene) compound can be converted to an acid chloride by contacting the carboxylate-substituted (arylcyclobutene) compound with thionyl chloride and refluxing at 70° C. to 80° C. The acid halide-substituted (arylcyclobutene) so formed can be used to prepare the monomers useful in this invention, as described hereinafter. In the embodiment wherein the aryl moiety is a benzene ring, the product corresponds to the formula

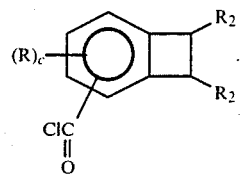

In an alternative synthesis, an aryl compound with ortho dibromomethyl groups can be converted to a 1,2-diiodoarylcyclobutene, by contacting the aryl compound substituted with ortho dibromomethyl moieties with an alkali metal iodide in an alkanol solvent at reflux so as to form the diiodoarylcyclobutenes. The product can be recovered by filtering, evaporating the filtrate and recrystallizing the product. In the embodiment wherein the aryl moiety is a benzene moiety, the starting material corresponds to the formula

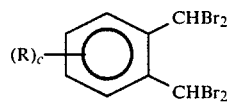

and the iodobenzocyclobutene can correspond to the formula

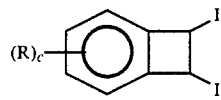

The 1,2-diiodoarylcyclobutenes can be converted to arylcyclobutenes by dissolving the 1,2-diiodoarylcyclobutenes in an alcohol solvent, preferably methanol or ethanol and contacting the solution with an alkali metal hydroxide in the presence of a palladium-on-carbon catalyst and $H_2$ gas at a temperature of 20° C. to 30° C. In general, at least between about 2 and 4 moles of alkali metal hydroxide per mole of 1,2-diiodoarylcyclobutene is used. Preferably, between about 50 and 200 psi of hydrogen gas is used. The arylcyclobutenes prepared in this manner can be recovered by distillation. In the embodiment wherein the aryl moiety is a benzene moiety, the product corresponds to the formula

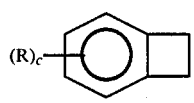

The arylcyclobutene can thereafter be brominated. In this process, the arylcyclobutene is dissolved in acetic acid and contacted with a brominating agent of pyridinium perbromide hydrobromide in the presence of mercuric salts, for example, mercuric acetate, at a temperature of between about 20° C. and 50° C. The brominated product can be recovered by extraction and distillation. In the embodiment wherein aryl moiety is benzene, the product corresponds to the formula

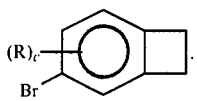

The brominated arylcyclobutene can thereafter be carbonylated to prepare a hydrocarbyloxy carbonyl-substituted arylcyclobutene. This carbonylation is achieved by dissolving the brominated arylcyclobutene in an alkanol solvent, and thereafter contacting the solution with carbon monoxide under pressure in the presence of a palladium catalyst, wherein the palladium is in the zero valence state, in the further presence of an acid acceptor under conditions such that the bromi-nated arylcyclobutene compound undergoes carbonylation. Preferred catalysts are complexes prepared from palladium acetate and triphenyl phosphine, palladium triphenyl phosphine tetrakis, and bis(triphenyl phosphine) palladium chloride complex. The acid acceptor is generally a tertiary amine. In general, the reaction vessel is pressurized with carbon monoxide to a pressure of between atmospheric and 3000 psi, preferred pressures are between 600 and 1000 psi.

This process is preferably performed at a temperature of between 100° C. and 140° C., most preferably between 120° C. and 130° C. The hydrocarbyloxy carbonyl arylcyclobutene can be recovered by filtering off the catalyst, washing away the acid scavenger with a 10 percent strong mineral acid solution, stripping off the solvent and distilling. To prepare a carboxamide-sub-stituted arylcyclobutene, a primary or secondary amine is substituted for the alcohol solvent. In the embodiment wherein the aryl moiety is a benzene moiety, the process corresponds to the following equation:

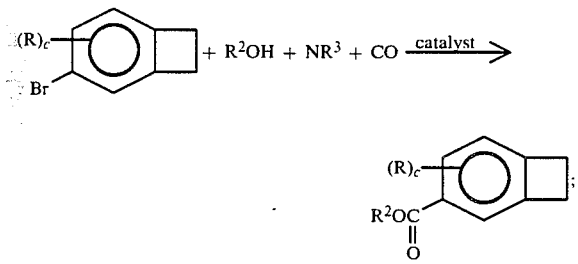

wherein R and c are as hereinbefore defined and $R^2$ and $R^3$ are hydrocarbyl moieties. The hydrocarbyloxy carbonyl-substituted or carboxamide-substituted arylcyclobutenes can thereafter be acidified and converted to acid chlorides by the process described hereinbefore.

The chlorocarbonyl-substituted arylcyclobutene compounds can be converted to arylcyclobutene monomers by contacting the halocarbonyl-substituted arylcyclobutene compounds with active hydrogen-containing compounds. Active hydrogen-containing compound refers herein to any compound which contains a hydrogen atom bonded to an oxygen, sulfur, phosphorus or nitrogen atom. For the purposes of this invention, an active hydrogen-containing compound refers to a compound containing a hydrogen atom which, because of its position in the molecule, displays significant activity according to the Zerewitnoff test described by Woller in the *J. Am. Chem. Soc.*, 49, 3181 (1927). Illustrative of such active hydrogen moieties are —COOH, —OH, —NH$_2$, =NH, —CONH$_2$, —SH, and —CONH—.

Such active hydrogen-containing compounds include polyols, polyamines, polyimides, polymercaptans, polyacids and the like. To prepare a arylcyclobutene monomer wherein the linking group is an amide, one contacts the halo carbonyl arylcyclobutene with an amine or polyamine. To prepare an arylcyclobutene monomer wherein the linking group is an imide, the active hydrogen-containing compound is an amide or polyamide. To prepare a arylcyclobutene monomer wherein the linking group is an ester, the active hydrogen-containing compound is an alcohol. To prepare an arylcyclobutene monomer wherein the linking group is an anhydride, the active hydrogen-containing compound is an acid. The active hydrogen-containing compounds useful in this invention generally correspond to the formula B—(H)$_n$ wherein B and n are as hereinbefore defined. More preferably the active hydrogen-containing compound corresponds to the following formula X—Z—(H)$_n$ )

wherein X, Z and n are as hereinbefore defined.

An alternative method to prepare an arylcyclobutene monomer with an amido- or polyamido(hydrocarb-poly-yl)-bridging member involves reacting an amino or polyamino hydrocarbon with at least one equivalent of a hydrocarbyloxy carbonyl arylcyclobutene for each amino moiety on the hydrocarbon. The reactants are dissolved in an equal volume of 1,2,4-trichlorobenzene and heated to 170° C. for about 6 hours. The alkanol by-product generated can be removed by distillation or absorption on a molecular sieve. The solvent is removed by washing it away with ethyl ether. The product prepared results in an amide-linking group wherein the nitrogen atom is bound to the carbonyl moiety.

Another preparation of an arylcyclobutene compound follows the reaction that reported by Skorcz and Kaminski, *Org. Syn.*, 48, pages 53–56 (1968). In a typical preparation, an alkyl cyanoacetate is added to a solution of sodium metal in ethanol followed by the addition of an ortho-halomethylaryl halide. The alkyl 3-(O-haloaryl)-2-cyanopropionate is isolated and treated with aqueous sodium hydroxide. Subsequent acidification results in the cyanopropionic acid derivative. That derivative is placed into N,N-dimethylformamide and is refluxed to form the 3-(O-haloaryl)propionitrile derivative which is isolated and added to a suspension of sodamide in liquid ammonia. After an appropriate reaction time, ammonium nitrate is added and the ammonia allowed to evaporate. The cyanoarylcyclobutene is isolated by ether extraction and purified by fractional distillation under reduced pressure.

Substituted arylcyclobutenes can be prepared by the same technique by using the appropriately substituted reactants, such as an alkyl or alkoxybenzyl halide. Also substituents can result from using an alkyl haloacetate, alkyl acetoacetate or a dialkylmalonate.

In another preparation of an arylcyclobutene compound based on the paper by Matsura et al., *Bull. Chem. Soc. Jap.*, 39, 1342 (1966), o-aminoaryl carboxylic acid is dissolved in ethanol and hydrochloric acid added. Isoamylnitrite is slowly added to the cold stirred solution and diethyl ether is then added. The product, aryldiazonium-2-carboxylate hydrochloride, is filtered. That product is placed in a solvent, preferably ethylene dichloride, and acrylonitrile and propylene oxide is added to the stirred mixture which is then heated under nitrogen until the reaction is complete. After cooling, the mixture is filtered and the product, 1-cyanoarylcyclobutene, is isolated by fractionally distilling the filtrate under reduced pressure.

Amounts of reactants, reaction parameters and other details can be found in the cited article, the examples of this application, or can be easily deduced therefrom.

In a next sequence of reactions, the cyanoarylcyclobutene or substituted derivative is nuclear substituted. When the arylcyclobutene monomer to be prepared has an amide-linking group, the cyanoarylcyclobutene is aminated. In one preparation, the cyanoarylcyclobutene is added slowly to a cold solution of sodium nitrate in concentrated sulfuric acid to form 5-nitro-1-cyanoarylcyclobutene. That nitro compound is isolated, dissolved in ethanol and reduced by hydrogenation over a palladium on carbon catalyst. The isolated product is 5-amino-1-cyanoarylcyclobutene. In the preferred embodiment where the aryl moiety is benzene, the product corresponds to the formula

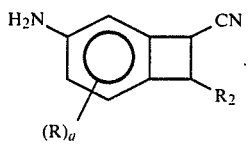

In another method of preparing the arylcyclobutene monomers, the amino-substituted arylcyclobutene is reacted with an appropriate coupling material. Coupling material refers herein to a compound which reacts with the amino or other substituent on the arylcyclobutene so as to form a bridging member with the amino or other substituent. Such processes are described hereinafter. In the embodiment wherein the bridging member contains amide-linking groups, the amino-substituted arylcyclobutenes are reacted with a polyvalent acid chloride. In practice, the amine-substituted arylcyclobutene is dissolved in a chlorinated aliphatic hydrocarbon solvent to which is added a tertiary amine, the acid acceptor, and thereafter the polyvalent acid chloride in a chlorinated aliphatic hydrocarbon solvent is added slowly to the mixture. This is preferably done at about 0° C. in an inert atmosphere. It is preferred to stir the reaction mixture for a period of time at 0° C. after the addition is complete.

To prepare a hydroxy-substituted arylcyclobutene, an amine-substituted arylcyclobutene is contacted with an alkali metal nitrite in the presence of sulfuric acid at 0° C., and thereafter the reaction mixture is heated to 100° C.

To prepare a mercapto-substituted arylcyclobutene, first an arylcyclobutene is reacted with chlorosulfonic acid to prepare an arylcyclobutene sulfonyl chloride. Arylcyclobutenyl sulfonyl chloride is reacted with zinc to prepare a mercapto-substituted arylcyclobutene. Alternatively, the arylcyclobutene is treated with a mixture of sulfur trioxide and dioxane at 0° C. followed by treatment with water. The arylcyclobutene-sulfonic acid is isolated and treated with phosphorous pentachloride to form the arylcyclobutene sulfonyl chloride which is then reduced with zinc to the mercapto-substituted arylcyclobutene.

An iodo-substituted arylcyclobutene can be prepared by reacting an amino-substituted arylcyclobutene with an alkali metal nitrite, sulfuric acid and potassium iodide at 0° C. under conditions such that an iodoarylcyclobutene is prepared.

An alkenyl-substituted arylcyclobutene can be prepared by reacting a bromo-substituted arylcyclobutene with an alkene, wherein the alkene contains a terminal olefin, in an aliphatic hydrocarbon solvent in the presence of a palladium catalyst such as palladium acetate, and a tertiary amine such as triethylamine. It is advantageous to use a slight excess of the bromo-substituted arylcyclobutene. The tertiary amine, which functions as an acid acceptor, is used in equimolar amounts with the bromo-substituted arylcyclobutene. The palladium catalyst is used in catalytically effective amounts. Generally this process can be performed at temperatures of between about 40° C. and 140° C.

To prepare an arylcyclobutene monomer with an alkene-poly-yl or alkenar-poly-yl-bridging member, an alkene or alkene-substituted aromatic compound which contains at least one terminal olefinic moiety is reacted with at least one mole of a bromo-substituted arylcyclobutene for each terminal olefin under conditions described hereinbefore.

To prepare an arylcyclobutene monomer in which the bridging member contains an amine-linking group, the amine-substituted arylcyclobutene is reacted with a compound which contains at least one alkyl halide moiety. In order to prepare an arylcyclobutene monomer in which the bridging member contains a linking group which is ureylene, the amine-substituted arylcyclobutene is reacted with a compound which contains at least one isocyanate or phosgene moiety.

To prepare an arylcyclobutene monomer in which the bridging member contains a linking group of a cyclic imide, the amine-substituted arylcyclobutene is reacted with a compound which contains at least one anhydride moiety.

To prepare an arylcyclobutene monomer with a polyvalent organic bridging member containing carbonyl-linking groups, the arylcyclobutene is reacted with an acid chloride with at least one acid chloride moieties, in the presence of aluminum chloride.

To prepare an arylcyclobutene monomer with a polyvalent organic bridging member containing an ammonium carboxylate-linking group, a carboxylate-substituted arylcyclobutene is contacted with a compound containing at least one polyamine-substituted moiety.

To prepare an arylcyclobutene monomer with a polyvalent organic bridging member containing thio-linking groups, a mercapto-substituted arylcyclobutene is reacted with an alkali metal hydroxide to prepare an alkali metal salt of the mercapto-substituted arylcyclobutene. The salt is then reacted with an organic compound containing at least one halo moiety to prepare an arylcyclobutene monomer with an organic bridging member containing thio-linking groups.

To prepare an arylcyclobutene monomer with a polyvalent organic bridging member containing nitrogen (amino)-linking groups, at least one equivalent of an amino-substituted arylcyclobutene are reacted with an organic compound containing at least one aldehyde moiety in the presence of an alkali metal cyanoborohydride under conditions that an arylcyclobutene monomer with a polyvalent organic bridging member with amino-linking moieties is prepared. One equivalent of amino-substituted arylcyclobutene for each aldehyde moiety on the organic aldehyde-containing compound is used. Alternatively, at least one equivalent of amine-substituted arylcyclobutene are reacted with an organic compound containing at least one bromo moiety in the presence of an alkaline earth metal carbonate under conditions such that an arylcyclobutene monomer with an organic bridging member containing amino-linking moieties is prepared. An equivalent of amino-substituted arylcyclobutene is used for each bromo moiety on the bromo-substituted organic compound.

To prepare arylcyclobutene monomers with polyvalent organic bridging members containing oxygen-linking moieties, a hydroxy-substituted arylcyclobutene is contacted with an alkali metal hydroxide to prepare an alkali metal salt of a hydroxy-substituted arylcyclobutene. At least one equivalent of the salt is then reacted with an organic compound containing at least one bromo moieties, under conditions such that an arylcyclobutene monomer with an organic bridging member containing oxygen-linking groups is prepared. One equivalent of the salt for each bromo moiety on the organic compound is used.

An alternative method of preparing the arylcyclobutene monomers wherein a carbonyl group is attached to the aryl moiety involves contacting the carboxylate-substituted arylcyclobutenes with 1',1-carbonyldiimidazole in an ether solvent at 0° C. The reaction mixture is then heated until it reaches the reflux of the solvent and thereafter any active hydrogen-containing compound is added so as to prepare a arylcyclobutene monomer, wherein the bridging member contains a carbonyl group which is bonded to the aryl group of the arylcyclobutene.

In order to prepare a polysiloxane bridging member, the amino-substituted arylcyclobutene is reacted with a polychlorinated polysiloxane. Alternatively, a halocarbonyl-substituted arylcyclobutene is reacted with an aminoalkylterminated polysiloxane.

To prepare an arylcyclobutene monomer with a polyvalent organic bridging member comprising a carbonyl moiety, an acid-halide-substituted (arylcyclobutene) is reacted with an arylcyclobutene in the presence of $AlCl_3$ or $SnCl_4$.

To prepare an arylcyclobutene monomer with a carbonyldioxy inorganic bridging member, at least one and preferably two moles of a hydroxy-substituted arylcyclobutene is reacted with phosgene in the presence of a tertiary amine. To prepare an arylcyclobutene monomer with a bridging member of a polyvalent metal ionically bonded to a polyvalent carboxylate moiety, a carboxylate-substituted arylcyclobutene is reacted with a metal hydroxide to prepare a metal poly(arylcyclobutene) carboxylate. In general, the metal hydroxide is reacted with the number of moles of carboxylate-substituted arylcyclobutenes equal to the metal's coordination number. An arylcyclobutene monomer with a polyvalent metal bridging member is prepared by first reacting one equivalent of a bromine-substituted arylcyclobutene with one equivalent of magnesium in an ether solvent to prepare an arylcyclobutenyl magnesium bromide. To prepare a di(arylcyclobutenyl) magnesium, one equivalent of a brominated arylcyclobutene is reacted with one equivalent of magnesium. The arylcyclobutenyl magnesium bromide is reacted with a metal chloride to prepare an arylcyclobutenyl metal. The metal chloride is reacted with the number of equivalents of arylcyclobutenyl magnesium bromide equal to the metal's oxidation state.

To prepare an arylcyclobutene monomer with an inorganic bridging member of sulfur, a mercapto-substituted benzocyclobutene is reacted with an iodo-substituted arylcyclobutene in an amide solvent in the presence of an alkali metal hydroxide. Alternatively, the mercapto-substituted arylcyclobutene can be reacted with cuprous chloride to prepare a cuprous salt of a mercapto-substituted arylcyclobutene. The salt can thereafter be reacted with an iodo-substituted cyclobutene in an amide solvent to prepare an arylcyclobutene monomer with a sulfide bridging member. The sulfide bridging member can be converted to a sulfoxide by contacting the arylcyclobutene sulfide with one equivalent of peracetic acid under conditions to oxidize the sulfide to a sulfoxide. Alternatively, the sulfide can be converted to a sulfone by contacting the arylcyclobutene with at least two equivalent of peracetic acid under conditions to oxidize the sulfide to a sulfone.

To prepare an arylcyclobutene monomer with a phosphorus bridging member, an arylcyclobutene magnesium bromide is reacted with phosphorus trichloride to prepare a tri(arylcyclobutenyl) phosphine. The tri(arylcyclobutenyl) phosphine can be contacted with peracetic acid, so as to prepare a tri(arylcyclobutenyl) phosphine oxide.

To prepare an arylcyclobutene monomer with a nitrogen bridging member, an amino-substituted arylcyclobutene is reacted with a potassium hydride to prepare a potassium salt of an amine-substituted arylcyclobutene. The salt is then reacted with an iodoarylcyclobutene in liquid ammonia under ultraviolet light, under conditions that an arylcyclobutene with a nitrogen bridging member is prepared.

To prepare an arylcyclobutene monomer with an oxygen bridging member, at least one, and preferably two, equivalents of a hydroxy-substituted arylcyclobutene are reacted with cupric carbonate to prepare cupric salt comprising a copper cation and two anions of hydroxyarylcyclobutenes from which the hydroxyl hydrogens have been abstracted. The salt is then reacted with an iodoarylcyclobutene, at between 100° C. and 180° C., either neat or in an amide solvent, under conditions such that a di(arylcyclobutene) ether is prepared.

The arylcyclobutene monomeric compositions are useful in preparing polymeric compositions. In general, polymeric compositions can be prepared by subjecting the monomeric compositions to polymerization conditions. Typically, such conditions can include subjecting the monomeric compositions to radiation such as, for example, gamma-, electron-beam, ultraviolet, and thermal radiation. Thermal radiation is preferred because of its ready application. As described above, an arylcyclobutene polymeric composition comprises an arylcyclobutene monomer in polymerized form. The arylcyclobutene monomer can be a mono- or a poly(arylcyclobutene) monomer. The polymeric composition can also contain copolymerized monomers, and other compositions such as, for example, fillers, miscible compositions and the like. The arylcyclobutene monomeric composition can be polymerized by heating to the polymerization temperature of the particular monomer(s) used. The polymerization is an addition polymerization wherein no volatiles are generated. Furthermore, no catalyst initiator or curing agents are necessary for the polymerization to take place. However, in some cases employing a metal catalyst composition can lower the polymerization and cure temperature. Suitable compositions include copper catalysts and the like. It is believed that the polymerization takes place when the cyclobutene ring undergoes transformation to prepare a molecule resembling a 1,3-cyclohexadienyl moiety with two exo-olefinic unsaturated moieties adjacent to one another wherein each of the olefinic unsaturated moieties undergoes reaction with the olefinic unsaturated moieties of other 1,3-cyclohexadienyl-containing molecules which have undergone the same transformation as well as other moieties which undergo addition polymerization reactions. The temperature at which the arylcyclobutene monomers undergo polymerization is affected by the nature of any substituent on the cyclobutene ring. In some embodiments, the temperature of polymerization is as low as about 30° C. In preferred embodiments, the temperature at which polymerization is initiated is above 150° C., more preferably above about 200° C. It is to be noted that the temperature at which polymerization is initiated is dependent upon the nature of substituents on the cyclobutene ring. In general, wherein the cyclobutene ring is unsubstituted, the polymerization is initiated at about 200° C. Wherein the cyclobutene ring is substituted with an electron-donating substituent, the polymerization temperature is generally lowered, the higher the ability of the substituent to donate electrons, the lower the polymerization initiation temperature is. Conversely, the electron-withdrawing substituents on the cyclobutene ring result in higher polymerization initiation temperatures. The unsubstituted cyclobutene in general polymerizes at the highest temperature.

It is believed the polymeric compositions prepared from the arylcyclobutenes monomeric compositions comprise units which can correspond to the formulae

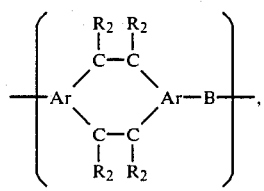

A and

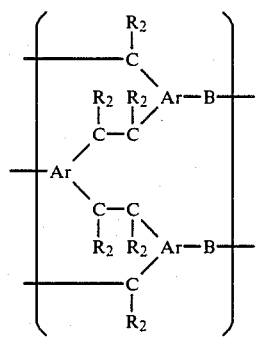

B and mixtures thereof. It is believed that the preferred polymeric compositions prepared from the arylcyclobutenes monomeric composition comprise mixtures of formulae A and B.

In those embodiments wherein Ar is benzene, it is believed that the polymeric compositions prepared from benzocyclobutene monomeric compositions comprise units which can correspond to the formulae

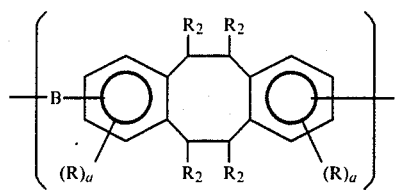

C and

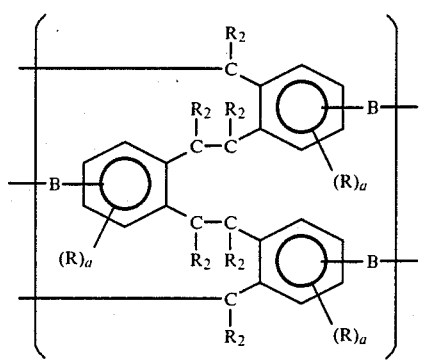

D and mixtures thereof. It is believed the preferred polymer compositions prepared comprise mixtures of formulae C and D with D being predominant.

The method of polymerization of the arylcyclobutene monomeric composition has a significant effect on the nature and properties of the polymeric composition prepared. In one embodiment, the arylcyclobutene monomeric compositions of this invention can be melt polymerized. The melt polymerization of arylcyclobutene monomeric compositions is useful to prepare solid parts, coatings, composites, adhesives and fibers.

In one embodiment of the melt polymerization, the monomeric composition can be heated above its melting temperature to provide a molten liquid. Such a temperature typically can range between about 80° C. and 200° C. The liquid can thereafter be poured or injected into a mold. Advantageously, the mold is treated with a suitable mold release agent, and pressure can be applied on the melted monomeric composition in the mold. Generally, pressures of between about 100 and 2000 psi are suitable. Thereafter, the monomeric composition can be heated to a temperature and time sufficient to polymerize and cure the composition. Such a temperature typically can range between about 200° C. and 300° C., preferably between about 200° C. and 250° C. and the time typically can range between about 10 minutes and 3 hours. Upon cooling, the polymeric composition can be removed from the mold.

Polymeric compositions prepared in this manner can subsequently be thermally treated at temperatures above 200° C. to raise the modulus and lower the coefficient of expansion of such polymeric compositions.

In general, the polymeric compositions prepared by this method are insoluble in many organic and aqueous solvents. They can swell but do not dissolve, are thermally stable at 300° C., have a good modulus, a low water pickup and are reasonably hard.

Suitable fillers and reinforcing materials can be, generally, in any powder form and/or fibrous products, for example, of the type commonly used in the production of moldings based on unsaturated polyester resins or epoxide resins. Examples of products such as these are, primarily, granular fillers such as quartz powder, ground shale, asbestos powder, powdered carborundum, chalk, iron powder, aluminum powder, sand, gravel and other fillers of this kind, also inorganic or organic fibers, more especially glass fibers in the usual textile forms of fibers, filaments rovings, yars, nonwovens, mats and cloths, etc. In this connection, amino silane-based finishes have proven to be particularly effective. It is also possible to use corresponding textile structures of organic, preferably synthetic fibers (polyamides, polyesters) or on the basis of quartz, carbon, metals, etc., as well as monocrystals (whiskers).

The monomeric compositions can be combined with fillers or reinforcing materials for use in particular in vessel and pipe construction by the winding technique, in electrical engineering, in mold construction and tool making and also in the construction of heavily stressed components, in the lightweight construction of vehicles in aeronautical and astronautical engineering.

In another embodiment, the arylcyclobutene monomeric compositions can be used to prepare coatings and films. In one embodiment, the monomeric composition can be dissolved in a suitable solvent and coated onto the substrate of choice. Thereafter the coated substrate is treated at temperatures of above the polymerization temperature of the monomeric composition. Preferably, the polymerization temperature is 150° C. or above, more preferably 200° C. or above. The coated substance is subjected to polymerization temperatures for a sufficient time for the polymerization to be completed. Preferably, such exposure times are between 10 minutes and 10 hours. Suitable solvents are those which volatilize away at temperatures below the polymerization temperature. Preferred solvents are cyclic and aliphatic ethers, lower alkanols, amides, and chlorinated hydrocarbon solvents. It is preferable to saturate the solvent with the monomeric composition, a 20 to 30 weight percent concentration of monomeric composition in the solvent is more preferred.

The arylcyclobutene monomeric compositions can be combined with the powder-form or fibrous fillers or reinforcing materials either before or after preparing the partially polymerized composition. For example, it is possible to impregnate powder-form or fibrous fillers or reinforcing materials such as quartz sand or glass cloths, with the arylcyclobutene monomeric compositions, optionally in solution.

In another embodiment, a film can be prepared from the arylcyclobutene monomeric compositions by powder coating techniques. In particular, the monomeric composition in a powder form can be placed on a desired substrate. Thereafter, the monomeric composition can be heated to its melt temperature over a time sufficient to melt the monomeric composition and allow the melted monomeric composition to form a liquid coating on the substrate. Thereafter, the melted monomeric composition coated on the substrate can be subjected to temperatures at which the monomeric composition polymerizes for a time sufficient for the monomeric composition to form a polymeric film on the desired substrate.

In another embodiment, the arylcyclobutene monomeric composition can be polymerized by solution polymerization techniques. In this embodiment, the monomeric composition can be dissolved in dipolar aprotic solvents with boiling points near or above the polymerization temperature of the monomeric composition. It is preferable that the solvents have a boiling point of near or above 200° C. and more preferable that the solvents have a boiling point of above 250° C. Examples of preferred dipolar aprotic solvents include amides and sulfones. It is necessary to add to the solution lithium salts which solubilize the polymeric composition in the solvents, preferably, between about 5 and 20 weight percent based on the solvent weight. A preferred lithium salt is lithium chloride. The polymerization takes place by heating the polymerization solution to a temperature at which the monomeric composition undergoes polymerization, preferably above 200° C. The polymerization time is preferably between about 1 and 10 hours. The polymeric composition can be recovered by adding water to precipitate the polymeric composition from the reaction solution and thereafter stripping off the solvent. The polymeric composition prepared with this method can be used in compression moldings or to prepare coatings.

In another embodiment, the arylcyclobutene monomeric composition which undergo polymerization at a temperature which is below the melting point of the monomeric composition can be polymerized in a solid state polymerization. In this method, the monomeric composition is heated to a temperature at which polymerization takes place. Polymeric compositions prepared in this method can be useful in the preparation of bearings, seals and other parts by powder metallurgy techniques.

It is advantageous for many uses of the arylcyclobutene monomeric compositions to employ the compositions in a partially polymerized or prepolymer form. To form the prepolymer, arylcyclobutene monomeric compositions can be contacted in an inert atmosphere or under vacuum and heated to a stage at which the polymerization mixture is sufficiently viscous or more manageable for end uses, such as in conventional moding equipment. Preferably, the monomeric composition can be treated at a temperature of 190° C. to 220° C. for between about 1 to 120 minutes. Thereafter, the partially polymerized composition or prepolymer can be used in various techniques to prepare cured polymeric compositions. In one preferred embodiment, the prepolymer composition can be cooled to form a powder which can be used to form compression molded articles, as an adhesive, and in many other uses.

In another embodiment, a partially polymerized composition or a prepolymer of the arylcyclobutene monomeric composition can be prepared by precipitation polymerization. In particular, the technique involves heating such monomeric composition in a solvent to prepare a low molecular weight partially polymerized composition or prepolymer. A solvent is used in which the monomers of the monomeric composition are soluble, but in which the prepolymer composition is insoluble. The mixture is subjected to sufficient polymerization conditions. As the prepolymer composition forms, it precipitates and can be removed. The prepolymer composition can be employed in many end uses to provide a cured polymeric composition. For example, the prepolymer composition can be fabricated in a hot compression mold which reacts out the remaining arylcyclobutene rings to give a thermoset polymeric composition. The partially polymerized prepolymer composition can be a fine white powder. Preferable solvents are nonpolar solvents, such as aromatic hydrocarbons, aliphatic hydrocarbons, aliphatic chlorinated hydrocarbons, aromatic chlorinated hydrocarbon solvents, biphenyls, diphenyl oxides, naphthalenes or polychlorinated biphenyls. In general, the monomeric composition can be dissolved up to saturation in the solvent used. A 20 to 30 percent by weight solution of the monomeric composition in the solvent is preferred. The prepolymer composition is used to prepare a polymeric composition by heating the prepolymer composition in the desired form, to the polymerization temperature of the monomeric composition for a time sufficient for the polymerization to go to completion.

The polymerization preferably takes place at temperatures of between about 200° C. and 250° C. for periods of between about 1 and 5 hours.

According to the method of this invention, the arylcyclobutene monomeric compositions can be used as adhesives. In such embodiment, a solid substrate to be joined to a second solid substrate can be contacted with the monomeric composition, for example, the monomeric composition in a powdered form. Thereafter, the second substrate to be adhered to the first is contacted with the first substrate having on the surface thereof a functionally effective amount of the monomeric composition. The substrates and monomeric composition are subjected to suitable bonding conditions. Such conditions can include a sufficient pressure to ensure contact of the substrates with the monomeric compositions and temperature to polymerize the monomer. For example, sufficient pressure of at least 1 psi can be applied and the monomeric compositions and substrates can be raised to a temperature at which the monomeric composition undergoes polymerization.

A functionally effective amount of the arylcyclobutene monomer is employed in the monomeric composition. Such an amount is an amount sufficient to adhere the first substrate to the second substrate under conditions of ordinary use and under the polymerization conditions. Conditions of ordinary use can differ according to the particular use and the functionally effective amount will consequently vary.

The monomeric composition can be applied to the first substrate in any effective manner. Typically, the monomeric composition can be in a powder or liquid form. When applied as a powder, the powder typically melts under polymerization conditions to a liquid and upon polymerization, and preferably curing, bonds the first substrate to the second substrate. Advantageously, the powder monomeric composition is first subjected to polymerization conditions to partially polymerize the monomeric composition. The partially polymerized composition can then be applied to the first substrate, the second substrate contacted and the contacted substrates subjected to curing conditions to bond the substrates together.

The second substrate is contacted to the first substrate in any effective manner. All that is required is that the bonding amount of monomeric composition contact the surface of both substrates.

Suitable bonding conditions are those conditions sufficient to polymerize and cure the monomeric composition such that the second substrate is attached through the adhesive composition to the first substrate. Typically, the bonding conditions will include polymerization conditions and pressure to maintain the contact. Typically, at least one pound, preferably at least five pounds, and more preferably at least ten pounds per square inch is required to maintain contact although any effective pressure can be employed. Higher pressures are preferred because such pressures can decrease the occurrence of voids in the bond; however, too high a pressure will force the melted monomeric composition from the joint. Therefore, it is advantageous to employ the arylcyclobutene monomer in the partially polymerized form. The cured polymeric composition exhibits a substantially reduced amount of volumetric shrinkage from the partially polymerized form. Thus, the danger of voids occurring is reduced. Also, the partially polymerized composition exhibits a substantially higher viscosity over the melted monomeric composition. Thus, more pressure can be applied to the substrates. The polymerization conditions can vary and can include subjecting the substrates to radiation such as, for example, gamma-, electron-beam, ultraviolet, and thermal radiation. Thermal radiation is preferred because of its ready application and versatility. Typically, such thermal radiation can vary, and can range from about 150° to about 300° C., preferably from about 225° to about 275° C.

The adhesion of the adhesive composition to the substrates can be improved by conventional surface treatment of the substrates and by employing a coupling agent. Typically, surface treating the substrates can be done by solvent cleaning; etching; mechanical treatments; and chemical modification. Suitable solvents for solvent cleaning include solvents which can remove dirt and impurities from the substrate's surface. Examples of such solvents include chlorinated solvents, acids, bases, hydrocarbons, and the like. Etching is done to chemically scratch the surface of the substrate. Examples of suitable etching materials and processes include acids; bases; oxidizing agents such as chromates and nitrates; phosphating; plasma; flame; electrical corona; and the like. Mechanical treatments to physically scratch the surface include, for example, sanding, wire brushing, sandblasting, filing, and the like.

Coupling agents are compositions which can bond to the substrate and the adhesive. Preferably, the coupling agent is chemically reactive with the adhesive composition. Suitable chemically reactive coupling agents comprise groups which can undergo addition polymerization reaction, such as vinyl groups.

Such adhesion improvement techniques can be employed individually or in combination with each other. Typically, the substrate can first be cleaned and then etched. A coupling agent can be applied, and is then dried or cured. The adhesive composition comprising the arylcyclobutene monomeric composition can then be applied. The second substrate, which can be similarly treated, can then be contacted with the first substrate. The adhesive composition is then subjected to conditions sufficient to bond the substrates together. The surface treating and coupling agent can improve the effectiveness of the adhesive by as much as two times or more.

The arylcyclobutene polymeric compositions can exhibit dielectric constants of lower than 3.5 and lower than 2.5. Therefore, such compositions are desirably employed in the electronics industries as die attach materials. In preparing die attach materials, electrical and preferably a thermal conductive metal composition is employed in the monomeric composition. An electrical conductive metal composition is a composition containing a metal which is known to conduct electricity. Preferably, the metal composition also is a thermal conductive metal composition. Such a composition contains a metal which is known to conduct heat. Such metals include, for example, gold, silver, copper, mixtures, and the like. Preferably, gold is employed because of its electrical and thermal conductivity. Typically, such metal will be in powder form. Therefore, in preparing the partially polymerized embodiment of this invention, a slurry of the metal powder in the liquid partially polymeric composition can be provided. Such a method is preferred because the viscous nature of the liquid partially polymerized composition aids the suspension and dispersion of the powder. An electrical and/or thermal conductive amount can be employed. Such an amount is an amount sufficient to contact the circuits to the board or other circuits through the chip. Such an amount can vary and typically ranges from about 50 to 70 percent, although any conductive amount can be employed. The arylcyclobutene adhesive can then be used as conventional die attach materials are used.

SPECIFIC EMBODIMENTS

The following examples are included for illustrative purposes only, and do not limit the scope of the invention or the claims. Unless otherwise specified, all parts and percentages are by weight.

Preparation of Arylcyclobutene Compounds

A. Preparation of 4-Carbomethoxybenzocyclobutene

A solution of methyl para-toluate (30 g, 0.20 mole) in 1,2-dichloroethane (80 ml) is added to a flask equipped with ice bath, stirrer, water-cooled condenser, ice traps and scrubber. To the stirred solution is added chloromethyl methyl ether (48 ml, 0.63 mole), thionyl chloride (5.8 ml, 0.080 mole), and last ferric chloride (6.5 g, 0.040 mole) in two portions. The cooling bath is removed, and the stirred reaction mixture is heated at 60° C. (heating lamp, controller) for 3 hours.

Methanol (150 ml) is added gradually to the cooled reaction mixture (exotherm). Low boiling components are removed under vacuum. The solution of product in dichloroethane is washed with water, 5 percent sodium bicarbonate solution, dried over anhydrous magnesium sulfate, filtered, and solvent is removed under vacuum. The product contains 13 percent unreacted methyl para-toluate and 80 percent methyl 3-chloromethyl-4-methylbenzoate (CMMT-chloromethylated methyl toluate) as analyzed by capillary gas chromatography. Recovery of the starting material by vacuum distillation affords a distillation residue of 91 percent pure product (analysis by capillary gas chromatography).

The experimental pyrolysis unit is a quartz tube packed with quartz chips. The central portion of the tube is placed in a furnace. A 25-centimeter portion of the tube above the furnace serves as a preheating zone and the temperature in the middle of such preheating zone is between about 250° C. and 300° C. Attached to the top of the tube is an addition funnel. Attached to the bottom portion of the tube are cold traps and a means for pulling a vacuum on the tube. Methyl(3-chloromethyl)-4-methyl benzoate (50 g) is dissolved in 200 g of ortho-xylene and placed in the addition funnel. The furnace is heated up to 730° C. A vacuum pump is turned on and pressure is adjusted to 25 mm of mercury. The solution of methyl(3-chloromethyl)-4-methyl benzoate is added dropwise over a period of 1 hour and 15 minutes. Product and unreacted starting material are collected in cold traps. The pyrolytic tube is flushed with 200 ml of acetone after a cooling down period. The acetone solution is combined with the ortho-xylene solution collected in the cold traps. Acetone and ortho-xylene are distilled off through a 16-inch Vigreaux column under normal pressure. When most of the ortho-xylene is distilled, the system is brought to 0.02 mm mercury and 15.5 g of pure 4-carbomethoxybenzocyclobutene is collected at 61° C. The residue left in the distillation pot is methyl(3-chloromethyl)-4-methyl benzoate, 23 g.

B. Preparation of 1-Cyanobenzocyclobutene

A mixture of benzenediazonium-2-carboxylate hydrochloride (1.92 g), acrylonitrile (0.80 g) and propylene oxide (0.58 g) in 100 ml of ethylene dichloride is stirred in a flask under nitrogen at 50° C.–60° C. for 4 hours. The mixture is cooled to room temperature and filtered. The filtrate is examined by gas chromatography and is found to contain 0.52 g (40 percent yield) of 1-cyanobenzocyclobutene.

C. Preparation of 5-Amino-1-Cyanobenzocyclobutene

The 1-cyanobenzocyclobutene is added slowly to a cold solution of sodium nitrate in cold sulfuric acid. The so-formed nitro compound is isolated, dissolved in ethanol, and reduced by hydrogenation over a palladium on carbon catalyst.

D. Preparation of 1,2-Diiodobenzocyclobutene

In a 12-liter, three-neck flask equipped with two reflux condensers and an air-driven stirrer, is placed 6.5 liters of absolute ethanol. The system is connected to a nitrogen line and bubbler through a three-way valve. The system is purged with nitrogen and 437.5 g (1.037 moles) of $\alpha,\alpha,\alpha',\alpha'$-tetrabromo-o-xylene and 1,948.1 g (12.98 moles) of sodium iodide are added with stirring. The reaction mixture is stirred and heated under reflux for 10 days under nitrogen. The mixture is cooled and the ethanol solvent removed with a rotary evaporator. The residue is stirred with methylene chloride and filtered. The filtrate is extracted with water and then stirred for 15 minutes with a 20 percent sodium sulfite solution. The methylene chloride layer is separated and extracted 4 times with water. It is then dried over magnesium sulfate and filtered. The methylene chloride is then removed on a rotary evaporator and the residue is treated with hot methanol. The insoluble tarry impurities are separated by decantation and the methanol solution is treated with activated charcoal. The methanol-charcoal mixture is boiled for 15 minutes and then filtered through celite to remove the charcoal. The charcoal treatment procedure is then repeated 4 more times. Following this, the methanol filtrate is placed in a round-bottom flask and the methanol is removed on a rotary evaporator to give the crude product as a beige solid. This is recrystallized from methanol to give 166.9 g of pure product. The filtrate from the recrystallization is evaporated to give an orange oil which, on treatment with methanol, yielded another 62.9 g of pure product. Total yield is 233.8 g or 63.3 percent.

E. Bromination of benzocyclobutene

The brominating agent used in this case is pyridinium hydrobromide perbromide ($C_5H_5N^{\oplus}HBr_3^{\ominus}$, formula weight 319.86). This reagent is prepared just prior to its use via the method of Fieser, *Reagents for Organic Synthesis*, Fieser & Fieser, pp. 967–982.

A 2000-ml round-bottom, three-neck flask is equipped with a reflux condenser connected to a nitrogen line with T and mineral oil bubbler, mechanical stirrer, and a thermocouple attached to a temperature controller. The flask is then charged with 4.5 g of mercuric acetate (Hg(O$_2$CCH$_3$)$_2$, f.w. 318.68, 14.12 mmoles), 28.5 g of benzocyclobutene (C$_8$H$_8$, m.w.=104.15, 0.274 mole), and 950 ml of glacial acetic acid. This mixture is stirred, 60 g of pyridinium hydrobromide perbromide is added, and the reaction is heated to 50° C. After 4 hours, another 60 g of brominating agent is added The mixture is sampled and the conversion of starting material to product is monitored by gas chromatography. The addition of 60-g increments of brominating agent proceeds in this manner until conversion is complete (4 days, 460 g of pyridinium hydrobromide perbromide total).

The reaction product is isolated by first decanting the acetic acid solution into a separatory funnel and diluting with 500 ml of water. The crystals of pyridinium hydrobromide perbromide are then soaked in methylene chloride (250 ml) to leach out any residual product. This methylene chloride solution is decanted into the separatory funnel, the funnel shaken, and the layers separated. The aqueous solution is returned to the funnel and the process is repeated twice more. The methylene chloride extracts are combined and washed with 500 ml of Na$_2$SO$_3$ (5 percent), 500 ml of water, 500 ml of aqueous hydrochloric acid (10 percent), 500 ml of water, 500 ml of NaHCO$_3$ (saturated), 500 ml of water, and dried over MgSO$_4$. The methylene chloride is then carefully removed via distillation, and the product is isolated by vacuum distillation using a column packed with stainless steel mesh. 4-Bromobenzocyclobutene is collected at 58° C.-60° C. with a vacuum of 1.5 mm Hg. A total of 32.8 g of 4-bromobenzocyclobutene is isolated pure, and the pot residue contains another 8–10 g of material. Isolated yield is 65.6 percent of theoretical value.

F. Carbonylation of 4-Bromobenzocyclobutene to Prepare Carbomethoxybenzocyclobutene This reaction is run in a 450-ml Parr pressure reactor fitted with a magnetically coupled stirring system. Into this reactor is entered 30 g of 4-bromobenzocyclobutene (0.164 mole), 16.5 g of (CH$_3$CH$_2$)$_3$N (0.164 mole, freshly distilled over Na metal), 100 ml of CH$_3$OH (Burdick & Jackson brand), and the catalyst mixture of 1.1 g of Pd(O$_2$CCH$_3$)$_2$ (4.9 mmoles, 3 mole percent) and 1.1 g of PPh$_3$ (recrystallized from ethanol). The reactor is then sealed and attached to a CO cylinder. The mixture is purged with 600 psig CO three times while stirring, and finally pressurized and held at 600 psig CO. The temperature is raised to 125° C., and held under these conditions overnight (approximately 16 hours). After this time, the unreacted CO is vented, and the reaction vessel is cooled to ambient temperature. The methanol solution is diluted with 200 ml of water, and the product extracted with 3×150 ml of CH$_2$Cl$_2$. The methylene chloride solution is then washed with 250 ml of water, 250 ml of HCl (5 percent), 250 ml of water, 250 ml of NaHCO$_3$ (saturated), 250 ml of water, and dried over MgSO$_4$. The methylene chloride solution is checked for conversion by gas chromatographic analysis, and the composition is discovered to be 97 percent 4-carbomethoxybenzocyclobutene. The solvent is then removed by distillation, and the product is then purified by vacuum distillation at 66° C.-67° C., 1 mm Hg vacuum.

G. Preparation of Benzocyclobutene 4-Carboxylic Acid by Hydrolysis of 4-Carbomethoxybenzocyclobutene A 500-ml round-bottom, single-neck flask is equipped with magnetic stirrer and reflux condenser attached to a nitrogen line with T mineral oil bubbler. To this flask is added 10 g of 4-carbomethoxybenzocyclobutene (m.w. 162.19 g, 0.062 mole) and 190 ml of methyl alcohol (Burdick & Jackson brand). This solution is stirred, and to it is added 60 ml of aqueous NaOH solution containing 7.5 g of NaOH (m.w. 39.998, 0.188 moles). This mixture is stirred at room temperature for one hour, after which the solution is transferred into a 1000-ml separatory funnel. The strongly alkaline solution is first diluted with 250 ml of water, and washed with 250 ml of CH$_2$Cl$_2$. The aqueous solution is then drained into a large beaker and acidified with concentrated HCl until the solution is strongly acidic. A white precipitate forms upon acidification, and is extracted with 3×250 ml of CH$_2$Cl$_2$. The methylene chloride solution is dried over MgSO$_4$ and the solvent removed via rotary evaporation. The benzocyclobutene-4-carboxylic acid (8.95 g) is recovered as a white solid (98 percent of theoretical yield).

H. Preparation of Benzocyclobutene-4-Carboxylic Acid Chloride and Reaction Thereof With a Diamine 4-Carbomethoxybenzocyclobutene (29.2 g) is hydrolyzed to benzocyclobutene-4 carboxylic acid using the procedure given under Preparation G. The acid is dried and added to 50 ml of freshly distilled thionyl chloride in a 500-ml single-neck flask equipped with a reflux condenser, nitrogen blanket and magnetic stirrer. The mixture is refluxed under nitrogen for ½ hour. The excess thionyl chloride is removed under vacuum leaving the so produced acid chloride as a brown oil. The product weighs 28.6 g and is used without further purification. The acid chloride is dissolved in 100 ml of methylene chloride and added to a 2-liter three-neck flask equipped with a thermometer port (the 2-liter flask and accessories are dried with a heat gun prior to adding the acid chloride). The flask is then equipped with a reflux condenser topped with a nitrogen line and mineral oil bubbler, an addition funnel fitted with a septum and a thermocouple probe placed in the thermometer port. Triethylamine (20 g) is then added to the flask. Heptamethylene diamine (10.6 g) is weighed out into a bottle in a dry box and the bottle capped with a septum. The diamine is diluted with 100 ml of methylene chloride and transferred via a syringe to the addition funnel. The diamine solution is then added dropwise to the reaction mixture. After this addition, the addition funnel is filled with methylene chloride and this is also added to the reaction mixture. This rinsing procedure is then repeated a second time. Finally, the reaction mixture is heated at reflux for 16 hours. The mixture is cooled to room temperature and poured into a separatory funnel. The mixture is then washed successively with 500 ml of water, 500 ml of 5 percent hydrochloric acid, 500 ml of water, 500 ml of saturated sodium bicarbonate and finally dried over anhydrous magnesium sulfate. The methylene chloride is evaporated off to give the product as a light brown solid. This is diluted with 250 ml of toluene and heated. The solution is then filtered (after cooling for 15 minutes) and the solid removed through this filtration is again dissolved in 250 ml of toluene. This solution is also heated, cooled for 15 minutes and filtered (suction). The solid removed by this filtration shows no coloration upon dilution with toluene so the solid is removed by suction filtration and dried in vacuo. The final weight of the product is 24.58 g resulting in a 77.2 percent yield based on the amount of diamine added.

I Preparation of a Bisbenzocyclobutene Monomer Derived From a 1,n+2-Alkyldiacid

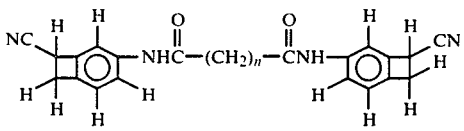

wherein n is the number of carbons between the carboxyl groups.

(a) n=2

5-Amino-1-cyanobenzocyclobutene (hereinafter called Compound A) (12.58 g, 0.089 mole) and triethylamine (7.05 g, 0.07 mole) are dissolved in 300 ml of methylene chloride. The solution is cooled to 0° C. in an ice bath, with stirring unger argon. A solution of 6.91 g (0.045 mole) of succinyl chloride in 100 ml of methylene chloride is added dropwise to the cooled solution. The reaction mixture is stirred for 30 minutes at 0° C. after the addition is complete. The reaction mixture is then warmed to room temperature and is poured into 400 ml of water. The mixture is extracted 3 times with 250-ml portions of methylene chloride. The combined methylene chloride extracts are washed once with 400 ml of a 5 percent hydrochloric acid solution. The methylene chloride layer is washed with 400 ml of water. Next, the methylene chloride solution is washed with 400 ml of saturated sodium bicarbonate and finally with 400 ml of water. The methylene chloride is removed under vacuum to give the product as a gray solid. Yield is 10 g or 60.6 percent.

(b) n=3

This monomer is prepared as under (a) using different amounts of reactants and is run in a nitrogen atmosphere. Compound A (12.13 g, 0.086 mole) and triethylamine (8.7 g, 0.086 mole) are dissolved in 300 ml of methylene chloride. Glutaryl chloride (6.61 g, 0.038 mole) is dissolved in 100 ml of methylene chloride and is added dropwise to the reaction mixture. The reaction is run and worked up the same as under (a) except that the methylene chloride solution is dried over anhydrous magnesium sulfate, filtered and then concentrated under vacuum. The product is a green solid. The yield is 13 g, 86.6 percent.

(c) n=4

This monomer is prepared in the same manner as described in (a) using different amounts of reactants and is run in a nitrogen atmosphere. Compound A (11.7 g, 0.083 mole) and triethylamine (8.4 g, 0.083 mole) are dissolved in 300 ml of methylene chloride. Adipoyl chloride (6.90 g, 0.038 mole) is dissolved in 100 ml of methylene chloride and is added dropwise to the mixture. The workup of the reaction mixture is the same as under (b), obtaining 14.7 g (98 percent) of a white solid.

The product is recrystallized from ethanol to give 8 g (53.3 percent yield) of solid.

(d) n=5

Thionyl chloride (5.12 g, 0.043 mole) is added dropwise under nitrogen to 20 ml of dry N,N-dimethylformamide which is cooled and stirred for 30 minutes at 0° C. in an ice bath. Pimelic acid (3.20 g, 0.020 mole) is dissolved in 15 ml of dry N,N-dimethylformamide and is added dropwise to the cooled reaction mixture. The reaction mixture is stirred an additional 30 minutes and then is warmed to room temperature and is stirred another 30 minutes, then again is cooled to 0° C. in an ice bath. Compound A (6.77 g, 0.047 mole) and triethylamine (6.06 g, 0.060 mole) are dissolved in 20 ml of dry N,N-dimethylformamide. This solution is then added dropwise to the cooled reaction mixture. The reaction mixture is slowly warmed to room temperature overnight. The reaction mixture is poured into 500 ml of water and is stirred for 30 minutes. Next, the water layer is extracted then washed twice with 200-ml portions of chloroform. The chloroform washes are combined and washed once with 300 ml of a saturated sodium bicarbonate solution, and once with 300 ml of water. The chloroform solution is washed once with 300 ml of a 10 percent hydrochloric acid solution and finally with 300 ml of water. The chloroform solution is then dried over anhydrous magnesium sulfate, filtered and concentrated under vacuum. The product obtained is column chromatographed over silica gel using ethyl acetate as the eluting solvent. A yellow colored solid is obtained.

(e) n=6

This monomer is prepared by the same procedure that is used under (d) except that 0.02 mole suberic acid was employed, and 0.048 mole of Compound A and 0.061 mole of triethylamine are dissolved in 15 ml of N,N-dimethylformamide and are added to the cooled reaction mixture. A white solid is obtained.

(f) n=7

This monomer is prepared by the method used under (d). Thionyl chloride (4.53 g, 0.038 mole) is added while stirring to 20 ml of dry N,N-dimethylformamide. Azelaic acid (3.33 g, 0.018 mole) is dissolved in 15 ml of N,N-dimethylformamide and is added to the reaction mixture at 0° C. The reaction mixture is then stirred as indicated previously under (d). Compound A (6.0 g, 0.042 mole) and triethylamine (5.37 g, 0.053 mole) are dissolved in 15 ml of N,N-dimethylformamide and added dropwise to the cooled reaction which is worked up as in (d), obtaining a brown solid.

(g) n=8

This preparation involves dissolving Compound A (1.41 g, 0.01 mole) and pyridine (1.0 g, 0.013 mole) in 35 ml of methylene chloride. This solution is cooled to 0° C. in an ice bath with stirring under nitrogen. Sebacoyl chloride (1.20 g, 0.005 mole) is dissolved in 15 ml of methylene chloride and is added dropwise to the cooled solution. The reaction mixture is stirred for 30 minutes at 0° C. and is warmed to room temperature. The reaction mixture is poured into 100 ml of water and is extracted 3 times with 50-ml portions of methylene chloride. The methylene chloride extracts are combined and washed once with 100 ml of a 5 percent hydrochloric acid solution. The methylene chloride solution is then washed with 100 ml of water and is dried over anhydrous magnesium sulfate. The solution is filtered and concentrated under vacuum to obtain a white-colored solid. The solid product is dried under a vacuum overnight.

J. Preparation of Bisbenzocyclobutene Monomer Containing a Diamido Bridging Member

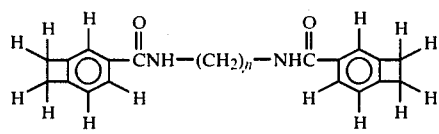

The general reaction sequence is to react compound (G), benzocyclobutene 4-carboxylic acid with 1,1-carbonyl diimidazole to give an imidazole derivative which is further reacted with a polyalkyene diamine to result in the bis-amide monomer.

(a) n=3

1,1-Carbonyldiimidazole (2.64 g, 0.016 mole) is dissolved in 45 ml of dry tetrahydrofuran and stirred under nitrogen at room temperature. The benzocyclobutene 4-carboxylic acid (2.37 g, 0.016 mole) is dissolved in 45 ml of dry tetrahydrofuran and added dropwise to the stirred imidazole solution at room temperature. The mixture is stirred for 30 minutes at room temperature and then heated at reflux overnight. The mixture is then cooled to room temperature and a solution of 1,3-diamino propane (0.53 g, 0.0072 mole) in 25 ml of dry tetrahydrofuran added dropwise. After this addition, the mixture is stirred at room temperature for 1½ hours and then, heated to reflux overnight. The mixture is cooled to room temperature and poured into 300 ml of water with stirring. The mixture is extracted with three 200-ml portions of methylene chloride. The methylene chloride extracts are combined and washed with three 400-ml portions of a 10 percent hydrochloric acid solution. Next, the methylene chloride extract is washed with one 500-ml portion of water followed by two washings with 400-ml portions of saturated sodium bicarbonate. Finally, the methylene chloride extract is washed with two 500-ml portions of water and dried over anhydrous magnesium sulfate. The magnesium sulfate is filtered off and the filtrate evaporated to yield 2.5 g of crude product. This is recrystallized from ethanol to yield 1.5 g (0.0045 mole) of pure product. The melting point of the product is 172° C.–178° C.

(b) n=5

The same procedure and workup is used as in the preceding example. The quantities of reactants and product are: benzocyclobutene 4-carboxylic acid (2.22 g, 0.015 mole); 1,1-carbonyldiimidazole (2.38 g, 0.0147 mole); 1,5-pentanediamine (0.72 g, 0.0071 mole); and product weight (1.8 g, 0.0049 mole). The melting point is 181° C.–185° C.

(c) n=6

The same procedure and workup is used as in the procedure where n =3. The quantities of reactants and product are: benzocyclobutene 4-carboxylic acid (2.22 g, 0.015 mole); 1,1-carbonyldiimidazole (2.43 g, 0.015 mole); 1,6-hexanediamine (0.79 g, 0.0068 mole); and product weight (0.65 g, 0.0017 mole). The melting point is 185° C.–194° C.

(d) n=7

The same procedure and workup is used as in the procedure where n =3. The quantities of reactants and product are: benzocyclobutene 4-carboxylic acid (2.22 g, 0.015 mole); 1,1-carbonyldiimidazole (2.48 g, 0.015 mole); 1,7-heptanediamine (0.99 g, 0.0076 mole); and product weight (0.6 g, 0.0015 mole). The melting point is 141° C.–145° C.

(e) n=8

The same procedure and workup is used as for the procedure where n=3. The quantities of reactants and product are: benzocyclobutene 4-carboxylic acid (1.48 g, 0.01 mole); 1,1-carbonyldiimidazole (1.62 g, 0.01 mole); 1,8-octanediamine (0.65 g, 0.0045 mole); and product weight (0.5 g, 0.0012 mole). The melting point is 172° C.–176° C.

K. Formation of a Bisbenzocyclobutene Ester Monomer Derived From Bisphenol-A

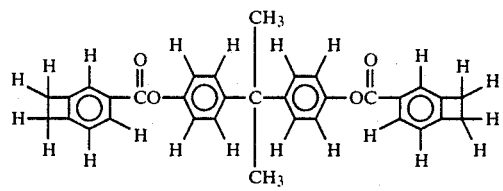

A 2000-ml three-neck, round-bottom flask is equipped with magnetic stirrer, 125-ml addition funnel, reflux condenser with nitrogen blanket, and stopper. To this system is added 25.62 g of 4,4'-isopropylidene diphenol (bisphenol A, m.w. 228.3 g, 0.1122 mole), 24.0 g of $(CH_3CH_2)_3N$ (0.238 mole, m.w. 101 freshly distilled over Na metal), and 600 ml of $CH_2Cl_2$ (Burdick and Jackson brand). This flask is now cooled with an ice water bath to 10° C., with stirring, and 38.78 g of benzocyclobutene 4-carboxylic acid chloride (m.w. 166.5 g, 0.233 mole) in 75 ml of $CH_2Cl_2$ is entered into the addition funnel. This solution is added dropwise to the stirring bisphenol A solution. When all of the acid chloride solution has been added, the addition funnel is washed with 2×100 ml of $CH_2Cl_2$ The reaction mixture is then allowed to stir overnight. The mixture is then entered into a separatory funnel and washed with 500 ml of water, 500 ml of HCl (5 percent), 500 ml of water, 500 ml of $NaHCO_3$ (saturated), 500 ml of water, and dried over $MgSO_4$. The mixture is then checked by HPLC to determine the relative purity of the monomer produced. The methylene chloride is removed via rotary evaporation and the resultant off-white solid is recrystallized from 600 ml of acetone. The first crop of white crystals is removed from solution via filtration and the solution remaining is concentrated to 250 ml and again recrystallized. The second crop of crystals is also isolated via filtration and the remaining solvent is removed to leave a light brown residue. Final weights and purity (by HPLC) are as follows: first crop, 42.10 g, 99.8 percent; second crop, 6.07 g, 99.3 percent; residue, 6.6 g. Yield is 88 percent of theoretical.

L. Preparation of Bisbenzocyclobutene Monomer Derived From an Olefinic Aromatic Compound Corresponding to the Formula

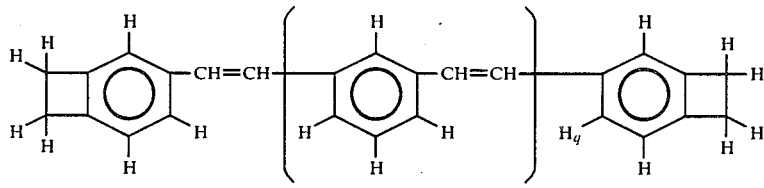

(a) q=3

A 25-ml flask equipped with a reflux condenser, nitrogen inlet, and magnetic stirring bar is charged with m-dibromobenzene (1.0 g, 4.2×10⁻³ m), m-divinylbenzene (2.75 g, 2.1×10⁻² m), tri-n-butylamine (8.4×10⁻³ m), tri-o-tolylphosphine (64 mg, 2.1×10⁻⁴ m), palladium (II) acetate (20 mg, 8.4×10⁻⁵ m), and acetonitrile (10 ml). The mixture is stirred under nitrogen and heated to reflux for 2 hours. The grey slurry is cooled to room temperature and stirred into 60 ml of 10 percent aqueous hydrogen chloride. The resulting precipitate is collected by filtration, washed with water, and air dried. This product is dissolved in ethylacetate, filtered, and the solvent evaporated to yield a yellow residue. Recrystallization of the residue from heptane gives 0.60 g (42 percent yield) of a compound of the formula

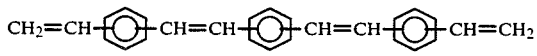

hereinafter referred to as determinal olefin, with a melting point of 105° C.

A 25-ml flask equipped with a reflux condenser, nitrogen inlet and magnetic stirring bar is charged with 4-bromobenzocyclobutene (1.5 g, 8×10⁻³ moles), the determinal olefin from part A (1.34 g, 4×10⁻³ moles), tri-n-butylamine (1.8 g, 9.7×10⁻³ moles), tri-o-tolylphosphine (62 mg, 4.0×10⁻⁴ moles), palladium II acetate (18 mg, 8.0×10⁻⁵ moles) and acetonitrile (5 ml). The reaction mixture is heated to reflux under nitrogen for 4 hours. The mixture is cooled to room temperature and stirred into 60 ml of 10 percent hydrochloric acid. The precipitate is collected by filtration, washed with water and air dried. The dried precipitate is then dissolved in 150 ml of boiling toluene, filtered hot and cooled to yield 310 ml of the product q=3. The monomer has a melting point of 180° C.-215° C.

(b) q=1

A 25-ml flask equipped with a reflux condenser, nitrogen inlet, and magnetic stirring bar is charged with 4-bromobenzocyclobutene (1.50 g, 8.0×10⁻³ m), m-divinylbenzene (4.0×10⁻³ m), tri-n-butylamine (1.8 g, 9.7×10⁻³ m), tri-o-tolylphosphine (62 mg, 4.0×10⁻⁴ m), palladium (II) acetate (18 mg, 8.0×10⁻⁵ m), and acetonitrile (5 ml). The reaction mixture is heated to reflux under nitrogen with stirring for 4 hours. The solidified mixture is cooled to room temperature and stirred into 60 ml of 10 percent aqueous hydrogen chloride. The resulting precipitate is collected by filtration, washed with water, and air dried.

The precipitate is dissolved in 75 ml of boiling ethylacetate, filtered hot, and cooled to yield 800 mg (60 percent) of the desired monomer with a melting point of 150° C.-152° C.

M. Qualitative Adhesion to a Glass Test Tube of Compound K Benzocyclobutene Derived From Bisphenol-A Ester The monomer is devolatilized at 100° C. and 0.5 mm Hg vacuum for two hours, cooled and the vacuum is backlet with nitrogen. The devolatilized monomer (0.5 g) is then transferred to a test tube with a ground glass joint, and equipped with a gas inlet tube topped with T and mineral oil bubbler for nitrogen blanket. The test tube is then placed in a Woods metal bath at 100° C. and slowly taken up to 250° C. The temperature of the Woods metal bath is held at between 245° C.-250° C. for 90 minutes. At the end of this time the test tube is removed from the bath and allowed to cool, still under nitrogen blanket. When cool to the touch, the gas inlet tube is removed and the polymer that remains in the tube is examined. The piece is light yellow in color, contains some voids, and cannot be fractured with a spatula to remove it from the tube.

N. Qualitative Adhesive qualities of the Bisbenzocyclobutene Polymer Derived From 1,7-Heptane-Dicarboxylic Acid

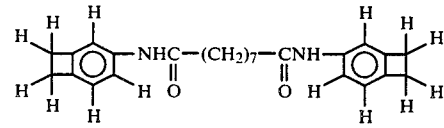

The monomer is prepared by reacting 4-amino-benzocyclobutene with 1,7-heptane-dicarboxylic acid in the presence of tetrahydrofuran. About 10 g of N,N'-carbonydiimidazole in 150 ml of tetrahydrofuran is added to a flask equipped with magnetic stirrer, condenser, and two dropping funnels. A solution of 1,7-heptane-dicarboxylic acid in tetrahydrofuran is provided by mixing about 6 g of the acid with 90 ml of the tetrahydrofuran. The solution is added dropwise to the carbonydiimidazole/tetrahydrofuran mixture, stirred for an hour and then heated to 60° C. for about 2.5 hours. The mixture is cooled to 25° C., and a 7.4 g of 4-aminobenzocyclobutene in 70 ml of tetrahydrofuran solution is added dropwise. The mixture is heated at 60° C. for 6 hours and then allowed to stand at room temperature overnight. The product is poured into water, giving a white precipitate which is extracted into methylene chloride. The organic solution is then washed with acid, water, base, water and the solvent is removed under vacuum. The product is dried at 70° to 80° C. under 1 to 2 mmHg for about 4 hours. The product is recrystallized from absolute ethanol, and is found to have a melting point of 163° to 165° C.

(i) Adhesion to Steel

A 0.3 g sample of the monomer is placed in a syringe which is loosely attached to a steel mold. The mold assembly is placed in an oven under positive dry nitrogen pressure. The oven is heated to 170° C. and held for about 20 minutes to provide a liquid monomer. The liquid monomer is injected into the mold. The assembly is heated to 253° C. and held there for about 3 hours. The assembly is then cooled to room temperature. Upon attempting to remove the polymer from the mold, the polymer adheres to the polished stainless steel sheets and shim. The sheets could not be pried loose after cooling on ice. The sheets are heated to 120° C. and are pried loose with cracking of the polymer.

(ii) Adhesion to Copper, Die Steel and Brass

A 2 mg sample of the monomer is placed in a copper cup. A 3 mg sample is placed in a die steel cup. A 2 mg sample is placed in a brass cup. The cups have ¼ inch diameter. The cups are placed in a positive nitrogen atmosphere and, after purging for 2 hours, the cups are heated to 250° C. The cups are held at that temperature for 3 hours and then allowed to cool slowly to room temperature. The polymer adheres very strongly to the copper and die steel cups and is moderately difficult to remove from the brass cup.

(iii) Adhesion Determinations to Various Substrates According to ASTM Standard D-3808, 1982 Volume. 22

A 50 mg sample of the monomer is applied to the substrates. The substrates are placed in an oven under an $N_2$ atmosphere. The oven is heated to 110° C. and held for 2 hours as nitrogen purging of the chamber occurs. The temperature is increased to 150° C. and the monomer is melted to a liquid phase. The assembly is heated to 202° C., held for 90 minutes; to 212° C., held for 20 minutes; to 220° C., held for 10 minutes; to 230° C., held for 10 minutes; and to 250° C., and held for one hour and 15 minutes. The substrates were then cooled slowly to room temperature.

For stainless steel, the polymer coating is gradually worked loose by force with a spatula at the edge of the coating. On an estimated difficulty scale of 0 to 10 (0=very easy, 10=not removed by force), is a 4. The edges chip upon removal.

For brushed cold rolled steel, the polymer coating is slowly forced loose from the panel with significant difficulty. Coating breaks into 2 pieces, with additional cracking. Estimated difficulty is about 60 to 7.

For aluminum, the polymer coating is pried loose with significant difficulty, and requires chipping at the edge and gouging the metal to give an intact piece of polymer. Estimated difficulty is 7.

For glass, the polymer coating breaks loose with moderate difficulty and breaks fragments of the glass. Estimated difficulty is about 5 to 6.

For brass, the polymer coating is gradually worked loose with hard prying, and chipping and breaking at the edges occuring. Estimated difficulty is 7.

For copper, the polymer coating is gradually forced loose with difficulty, and a large crack is formed in the coating. Estimated difficulty is 7.

O. Qualitative Adhesive Qualities of the Monobenzocyclobutene Derived From Maleimide

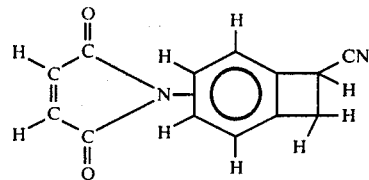

The monomer is prepared as follows. Into a 250 ml, three-necked flask equipped with a mechanical stirrer, reflux condenser, thermometer and nitrogen inlet is placed 11 g (0.045 mole) of N-[5-(1-cyanobenzocyclobutenyl)]maleamic acid, 2.4 g (0.03 mole) of anhydrous sodium acetate, and 45.94 g (0.765 mole) of fresh glacial acetic acid. The mixture is stirred and slowly heated under nitrogen until a clear yellow solution results (117° to 118° C.). After 5 minutes the heat is removed and the reaction mixture is allowed to cool under nitrogen overnight at room temperature. It is then slowly poured into a vigorously stirred slurry of ice and water (120 g total), and the resulting yellow precipitate filtered, washed with water until neutral to litmus, and transferred to a 500 ml beaker containing 150 ml of aqueous saturated sodium bicarbonate. This mixture is stirred for 10 minutes, then 150 ml of chloroform is added and stirred for an additional 10 minutes. The organic layer is taken up in three 50 ml portions of chloroform, and the solutions are combined and washed once with 150 ml of water. The chloroform solution is dried over anhydrous magnesium sulfate, filtered and evaporated on a rotary evaporator to give a viscous yellow oil. The product is pumped under vacuum over night to give a yellow solid that is purified by column chromatography on silica gel using 70 percent toluene/30 percent ethyl acetate as the eluent. The yield is 5.7 g equal to 56.5 percent. The melting point is 55° to 60° C.

A 0.3 g sample of the monomer in powder form is added to a syringe attached to a steel mold in an oven. Under a positive $N_2$ atmosphere, the oven is heated to 150° C. to melt the monomer and the viscous liquid monomer is injected into the mold. The oven is heated to 253° C. and held for 3 hours. The oven and assembly gradually cools to room temperature. Polished stainless steel plates do not adhere to the polymer. The polymer does adhere to the steel shim cavity and horizontal cracks occur upon removal from the shim.

P. Qualitative Adhesion to Various Substrates of Compound K, the Bisbenzocyclobutene Polymer Derived From Bisphenol-A The procedures and test methods of Procedure N(iii) are followed using the compound of preparation (K).

For cold rolled steel, the polymer coating is removed easily from the substrate and the estimated difficulty is 2.

For copper, the polymer coating breaks upon removal and the estimated difficulty is 3.

For glass, the polymer coating is easily removed from the glass and the estimated difficulty is about 0 to 1.

Q. Qualitative Adhesion to Various Substrates of the 1,2-Bisbenzocyclobutene Polymer Derived From Ethene

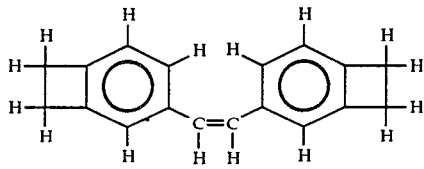

The monomer is prepared by heating a mixture of 4-bromobenzocyclobutene with 4-vinylbenzocyclobutene at reflux. Vinylbenzocyclobutene is prepared by adding 0.98 g of 4-bromobenzocyclobutene, 0.04 g palladium (II) acetate, and 0.17 g of tri-o-tolylphosphine to a mixture of 100 ml acetonitrile and 0.6 g of triethylamine in a 450 ml Parr pressure reactor. The reactor is pressurized with 250 psig ethylene. The mixture is heated to 125° C. and stirred for 16 hours. The apparatus is cooled and the remaining ethylene is vented. The product is washed with water and 5 percent hydrochloric acid and dried over $MgSO_4$. The solvent is removed to provide 4-vinylbenzocyclobutene. A 2.4 g sample of 4-bromobenzocyclobutene, a 1.7 g of 4-vinylbenzocyclobutene, a 2.4 g of tri-n-butylamine, a 100 mg of tri-o-tolylphosphine, 29 mg palladium (II) acetate and 10 ml acetonitrile are added to a fask equipped with a reflux condenser, nitrogen inlet, and magnetic stirrer. The reaction mixture is heated to reflux under nitrogen for 4 hours. The solution is cooled to room temperature and stirred into 60 ml of 10 percent hydrochloric acid solution. The precipitate is collected by filtration, washed with water and air dried. The product is recrystallized from ethylacetate and has a melting point of 132° to 133° C.

The procedures and test methods of Procedure N(iii) are followed using the bisbenzocyclobutene monomer derived from ethene.

For brushed cold rolled steel, the polymer coating breaks into several pieces and the edges of the coating remain on the substrate upon removal. The estimated difficulty is 4.

For copper, the polymer coating breaks off in small pieces during removal and appears to be rather brittle. The estimated difficulty is 5.

For glass, the polymer coating is easily removed and the estimated difficulty is about 0 to 1.

EXAMPLE 1

Polymerization of Compound (J) (d), the Bis-Benzocyclobutene Monomer Derived From 1,7-heptanediamine and Its Use as an Adhesive A one-inch square on the end of a steel coupon of 4 inches by 1 inch by 0.060 thickness is covered with powdered monomer prepared by the method described in Preparation (J) (d). This is overlapped with a second coupon of the same size. A one-inch square of the second coupon's end is covered with a powdered monomer and this is overlapped with a third coupon of the same size. These coupons are overlapped in a manner such that there is a one-inch square of each in contact with one of the others wherein powdered monomer is between the overlapped plates. A weight is placed on the joint and the plates are thereafter heated in an air oven at 250° C. for 1.5 hours. Thereafter the lap shear force needed to pull the coupons apart is measured. Table A demonstrates the joint thickness and lap shear of six such adhered coupons.

TABLE A

| Sample | Weight* (lb) | Average Joint Thickness (inches) | Lap Shear (lb) |
|---|---|---|---|
| 1 | 1 | 0.0075 | 4,600 |
| 2 | 1 | 0.0085 | 3,000 |
| 3 | 1 | 0.0075 | 3,100 |
| 4 | 7 | 0.006 | 2,900 |
| 5 | 7 | 0.005 | 3,300 |
| 6 | 7 | 0.004 | 3,700 |

*Weight on joint during curing.

EXAMPLE 2

Use of The Bisbenzocyclobutene Polymer Dervied from 1,7-Heptane-Dicarboxylic Acid as an Adhesive (i) Adhesive for Glass A 0.2 g sample of the monomer of preparation N in powder form is placed onto a glass slide. A second glass slide is placed on top of the first slide. The slides are heated at 254° C. for three hours. After cooling, the slides are separated after much force, breaking one of the slides, and a large amount of glass fragments is bonded to the polymer. The fragments and polymer are soaked in water and still could not be freed from the polymer.

(ii) Adhesive for Brass

A brass block with a 10/32 inch hole, a 10/32 inch bolt and a 10/32 inch nut are provided. A 30 mg sample of the monomer is placed around the bolt and the bolt is screwed loosely in place. The assembly is heated in an oven at 175° C. for about 45 minutes and the bolt is screwed tightly into the block so that the liquid monomer oozes up, out and around the block surface. The oven is heated to 250° C. and held for 3 hours. The oven is cooled slowly to room temperature. The bolt is opened with a torque wrench. The brass bolt head breaks off before opening.

EXAMPLE 3

Quantitative Adhesion to Various Substrates of Compound (J)(d) Bisbenzocyclobutene Polymer Derived From 1,7-Heptanediamine

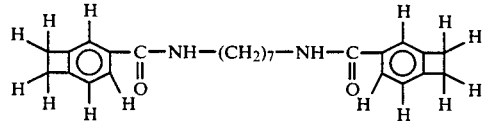

The monomer composition prepared from preparation (J)(d) is tested for lap shear strength at various temperatures. Solid substrates of 1 inch by 4 inches by 0.07 inch dimensions are bonded using the monomer at a thickness of about 0.005 inches. About 1 pound of force is used to hold the substrates together. The monomer is then heated to polymerization temperature to bond the substrates together. The monomer is used in powdered form, heated to about 250° C. for about 3 hours and cooled to room temperature. The bonded substrates are then pulled in a tensile testing machine to measure the force required to pull the substrates apart. The pull rate is 0.02 inches per second. Different sets of samples are run at 21° C., 50° C., 100° C. 150° C. and 200° C. The data is provided in the following tables.

(A) For a metal substrate of cold rolled steel, fifty samples are prepared having a layer of adhesive of about 0.005 inches. Ten samples each are teasted for lap shear at 21° C., 50° C., 100° C., 150° C. and 200° C. The results are provided in Table B.

TABLE B

| Samples[1] | Temperature (°C.) | Shear Force[2] (lbs) | Area of Joint (in²)[3] | Lap Shear[4] Pounds (psi) |
|---|---|---|---|---|
| 1 | 21 | 1,048 | 0.53 | 1,957 |
| 2 | 50 | 1,075 | 0.53 | 2,034 |
| 3 | 100 | 816 | 0.53 | 1,577 |
| 4 | 150 | 782 | 0.53 | 1,474 |
| 5 | 200 | 856 | 0.53 | 1,628 |

[1]Contain 10 samples each; however, one sample in 1, 2, 4 and 5 is rejected because the wrong sides of the substrate are bonded together and one sample in 1 and 2 are rejected because recorder was out of ink and no measurement was made.
[2]Average shear force required to separate the substrates.
[3]Determined by measuring the area of the adhesive after the substrates are separated.
[4]Average for the ten runs, determined according to the measurement for shear force and area of the joint.

(B) For a cold rolled steel substrate, at a pull rate of 2 inches per minute (as compared to a rate of 0.02 inches per minute above), the same procedure and test methods for (A) above are employed. The joint thickness varied between about 0.002 inches to about 0.006 inches. The results are provided in Table C.

TABLE C

| Samples | Temperature (°C.) | Shear Force (lbs) | Area of Joint (in²) | Lap Shear pounds (psi) |
|---|---|---|---|---|
| 1 | 23 | 693 | 0.52 | 1,332 |
| 2 | 50 | 770 | 0.52 | 1,493 |
| 3 | 100 | 678 | 0.51 | 1,338 |
| 4 | 150 | 676 | 0.52 | 1,312 |
| 5 | 200 | 522 | 0.52 | 1,013 |

(C) For aluminum substrates, the procedures and test methods of part (a) are followed to determine lap shear strength. The results are provided in Table (D) and Table (E).

TABLE D[1]

| Samples | Temperature (°C.) | Shear Force (lbs) | Area of Joint (in²) | Lap Shear pounds (psi) |
|---|---|---|---|---|
| 1 | 23 | 494 | 0.53 | 932 |
| 2 | 50 | 462 | 0.52 | 882 |
| 3 | 100 | 420 | 0.53 | 787 |
| 4 | 150 | 370 | 0.54 | 692 |
| 5 | 200 | 236 | 0.53 | 444 |

[1]Pull rate of 2 inches per minute.

TABLE E[2]

| Samples | Temperature (°C.) | Shear Force (lbs) | Area of Joint (in²) | Lap Shear pounds (psi) |
|---|---|---|---|---|
| 1 | 23 | 360 | 0.54 | 669 |
| 2 | 50 | 408 | 0.53 | 765 |
| 3 | 100 | 368 | 0.53 | 689 |
| 4 | 150 | 332 | 0.54 | 614 |
| 5 | 200 | 178 | 0.53 | 333 |

[2]Pull rate of 0.02 inches per minute.

What is claimed is:

1. A method of bonding a first solid substrate to a second solid substrate, said method comprising (a) applying a functionally effective amount of an arylcyclobutene monomeric composition to a surface of the first substrate,
(b) contacting said surface with a surface of the second substrate, and
(c) subjecting said monomeric composition to bonding conditions sufficient to bond the substrates.

2. The method of claim 1, wherein said arylcyclobutene monomeric composition comprises a monoarylcyclobutene monomer which corresponds to the formula

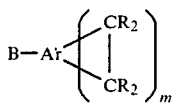

wherein
B is an ethylenically unsaturated hydrocarbon group or other moiety which is reactive with the cyclobutene ring of the arylcyclobutene moiety
Ar is an aryl moiety;
R is separately in each occurrence hydrogen, or an electron-withdrawing substituent or an electron-donating substituent; and
m is an integer of 1 or more.

3. The method of claim 1, wherein said arylcyclobutene monomer composition comprises a poly(arylcyclobutene) monomer which corresponds to the formula

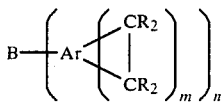

wherein
B is a direct bond, or bridging member;
Ar is an aryl moiety;
R is separately in each occurrence hydrogen, or an electron-withdrawing substituent or an electron-donating substituent;
m is an integer of 1 or more; and
n is an integer of 2 or more.

4. The method of claim 2, wherein said first substrate comprises a metal and said second substrate comprises a metal.

5. The method of claim 3, wherein said first substrate comprises a metal and said second substrate comprises a metal.

6. The method of claim 1, wherein said bonding conditions comprise applying a sufficient force to said substrates such that said amount of monomeric composition can contact both substrates and subjecting said monomeric composition to conditions sufficient to polymerize the monomeric composition.

7. The method of claim 2, wherein said bonding conditions comprise applying a sufficient force to said substrates such that said amount of monomeric composition can contact both substrates and subjecting said monomeric composition to conditions sufficient to polymerize the monomeric composition.

8. The method of claim 3, wherein said bonding conditions comprise applying a sufficient force to said substrates such that said amount of monomeric composimonomeric composition to conditions sufficient to polymerize the monomeric composition.

9. The method of claim 6, wherein said polymerization conditions comprise subjecting said monomeric composition to temperatures sufficient to polymerize the monomeric composition.

10. The method of claim 7, wherein said polymerization conditions comprise subjecting said monomeric composition to temperatures sufficient to polymerize the monomeric composition.

11. The method of claim 8, wherein said polymerization conditions comprise subjecting said monomeric composition to temperatures sufficient to polymerize the monomeric composition.

12. The method of claim 3, wherein said monomeric composition additionally comprises an electrical conductive metal composition in the form of a powder.

13. A method of bonding a first solid substrate to a second solid substrate, said method comprising
   (a) subjecting an arylcyclobutene monomeric composition to polymerization conditions for a time sufficient to provide a partially polymerized composition;
   (b) applying a functionally effective amount of said partially polymerized composition to a surface of the first substrate;
   (c) contacting said surface with a surface of the second substrate; and
   (d) subjecting said substrates and composition to sufficient bonding conditions.

14. The method of claim 13, wherein said arylcyclobutene monomeric composition comprises a monoarylcyclobutene monomer which corresponds to the formula of

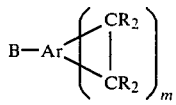

wherein
   B is an ethylenically unsaturated hydrocarbon group or other moiety which is reactive with the cyclobutene ring of the arylcyclobutene moiety
   Ar is an aryl moiety;
   R is separately in each occurrence hydrogen, or an electron-withdrawing substituent or an electron-donating substituent; and
   m is an integer of 1 or more.

15. The method of claim 13, wherein said arylcyclobutene monomer composition comprises a poly(arylcyclobutene) monomer which corresponds to the formula

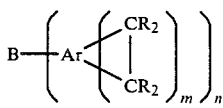

wherein
   B is a direct bond, or bridging member;
   Ar is an aryl moiety;
   R is separately in each occurrence hydrogen, or an electron-withdrawing substituent or an electron-donating substituent;
   m is an interger of 2 or more; and
   n is an integer of 2 or more.

16. The method of claim 14, wherein said first substrate comprises a metal, and said second substrate comprises a metal.

17. The method of claim 15, wherein said first substrate comprises a metal and said second substrate comprises a metal.

18. The method of claim 13, wherein said bonding conditions comprise applying a sufficient force to said substrates such that said amount of the partially polymerized composition can contact both substrates, and subjecting said monomeric composition to sufficient polymerization conditions.

19. The method of claim 14, wherein said bonding conditions comprise applying a sufficient force to said substrates such that said amount of monomeric composition can contact both substrates and subjecting said monomeric composition to sufficient polymerization conditions.

20. The method of claim 15, wherein said bonding conditions comprise applying a sufficient force to said substrates such that said amount of monomeric composition can contact both substrates and subjecting said monomeric composition to sufficient polymerization conditions.

21. The method of claim 16, wherein said polymerization conditions comprise subjecting said monomeric composition to sufficient polymerization temperatures.

22. The method of claim 14, wherein said polymerization conditions comprise subjecting said monomeric composition to sufficient polymerization temperatures.

23. The method of claim 15, wherein said polymerization conditions comprise subjecting said monomeric composition to sufficient polymerization temperatures.

24. The method of claim 15, wherein said monomeric composition additionally comprises an electrical conductive metal composition in the form of a powder.

25. The method of claim 3, wherein said polyarylcyclobutene monomer is a bisbenzocyclobutene monomer which corresponds to the formula

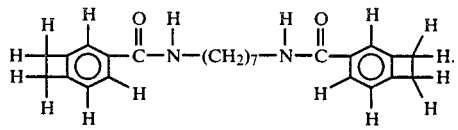

26. The method of claim 3, wherein said arylcyclobutene monomeric composition further comprises a monoarylcyclobutene monomer which corresponds to the formula

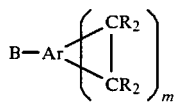

wherein
   B is an ethylenically unsaturated hydrocarbon group or other moiety which is reactive with the cyclobutene ring of the arylcyclobutene moiety
   Ar is an aryl moiety;
   R is separately in each occurrence hydrogen, or an electron-withdrawing substituent, or an electron-donating substituent, and
   m is an integer of 1 or more.

27. The method of claim 25, wherein said arylcyclobutene monomeric composition further comprises a mono-arylcyclobutene monomer which corresponds to the formula

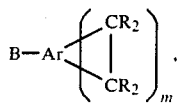

wherein

B is an ethylenically unsaturated hydrocarbon group or other moiety which is reactive with the cyclobutene ring of the arylcyclobutene moiety;

Ar is an aryl moiety;

R is separately in each occurrence hydrogen, or an electron-withdrawing substituent, or an electron-donating substituent, and m is an integer of 1 or more.

28. The method of claim 3, wherein said first substrate is a polymeric composition, and said second substrate is a polymeric composition.

29. The method of claim 3, wherein said first substrate is a polymeric composition, and said second substrate is a metal composition.

30. The method of claim 29, wherein said polymeric composition comprises a polyimide resin, and said metal composition comprises copper.

31. The method of claim 30, wherein said monomeric composition comprises a bisbenzocyclobutene monomer which corresponds to the formula

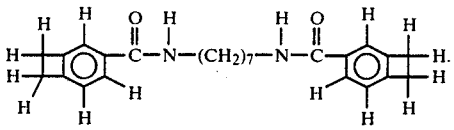

32. The method of claim 3, wherein said first substrate comprises silicon dioxide, and said second substrate comprises glass.

33. The method of claim 1, wherein step (a) further comprises subjecting said monomeric composition to polymerization conditions to provide a partially polymerized composition.

* * * * *

UNITED STATES PATENT AND TRADEMARK OFFICE
CERTIFICATE OF CORRECTION

PATENT NO. : 4,661,193

DATED : April 28, 1987

INVENTOR(S) : Robert A. Kirchhoff, et al.

It is certified that error appears in the above-identified patent and that said Letters Patent is hereby corrected as shown below:

Column 4, line 9, "sit" should be --site--.

Column 4, line 10, "noiety" should be --moiety--.

Column 4, line 32, "merber" should be --member--.

Column 8, line 52, "more" should be --most--.

Column 11, line 9, --those-- should be inserted after "include".

Column 16, line 22, the formula should read: $X(Z-H)_n$

Column 24, line 37, "moding" should be --molding--.

Column 37, line 53, "60" should be --6--.

Signed and Sealed this

Nineteenth Day of July, 1988

*Attest:*

DONALD J. QUIGG

*Attesting Officer*  *Commissioner of Patents and Trademarks*